(12) United States Patent
Barton et al.

(10) Patent No.: US 11,432,817 B2
(45) Date of Patent: Sep. 6, 2022

(54) PACKAGING FOR SURGICAL STAPLER BUTTRESS

(71) Applicant: Ethicon LLC, Guaynabo, PR (US)

(72) Inventors: Trevor J. Barton, Cincinnati, OH (US); Denise Griffiths, Hamburg (DE); John V. Hunt, Cincinnati, OH (US); Kevin O'Brien, Cincinnati, OH (US); Emily A. Schellin, Cincinnati, OH (US); Nicholas B. Van Stolk, Cincinnati, OH (US); Michael J. Vendely, Lebanon, OH (US)

(73) Assignee: Cilag GmbH International, Zug (CH)

( * ) Notice: Subject to any disclaimer, the term of this patent is extended or adjusted under 35 U.S.C. 154(b) by 304 days.

(21) Appl. No.: 16/235,541

(22) Filed: Dec. 28, 2018

(65) Prior Publication Data
US 2020/0205824 A1 Jul. 2, 2020

(51) Int. Cl.
| | | |
|---|---|---|
| *A61B 50/30* | (2016.01) | |
| *A61B 17/072* | (2006.01) | |
| *A61B 17/115* | (2006.01) | |
| *A61B 17/068* | (2006.01) | |

(52) U.S. Cl.
CPC ...... *A61B 17/07292* (2013.01); *A61B 17/115* (2013.01); *A61B 50/30* (2016.02); *A61B 2017/0688* (2013.01); *A61B 2017/07257* (2013.01); *A61B 2017/07271* (2013.01); *A61B 2017/07285* (2013.01)

(58) Field of Classification Search
CPC ...... A61B 17/07292; A61B 2017/0688; A61B 2017/07257; A61B 2017/07271; A61B 2017/07285; A61B 17/115

USPC .................................................. 227/175.1
See application file for complete search history.

(56) References Cited

U.S. PATENT DOCUMENTS

| | | | |
|---|---|---|---|
| 4,730,726 A | 3/1988 | Holzwarth | |
| 4,736,850 A | 4/1988 | Bowman et al. | |
| 4,805,823 A | 2/1989 | Rothfuss | |
| 4,961,498 A | 10/1990 | Kalinski et al. | |

(Continued)

FOREIGN PATENT DOCUMENTS

FR 2 876 086 A1 4/2006

OTHER PUBLICATIONS

U.S. Appl. No. 16/234,727, entitled "Surgical Stapler with Tissue Engagement Features Around Tissue Containment Pin," filed Dec. 28, 2018.

(Continued)

*Primary Examiner* — Chelsea E Stinson
*Assistant Examiner* — Mary C Hibbert-Copeland
(74) *Attorney, Agent, or Firm* — Frost Brown Todd LLC

(57) ABSTRACT

A packaging assembly is designed for an applicator that contains a buttress assembly that is used with a surgical stapler to reinforce a cut and stapled tissue site. The packaging assembly protects the buttress assembly from damage due to physical contact as well as exposure to adverse environmental factors like excess moisture, etc. In one example the packaging assembly includes a dual tray design with an inner tray that holds the applicator. The combined inner tray and applicator are hermetically sealed within a foil assembly or foil pouch. The foil pouch with the inner tray and applicator within is placed within the outer tray to protect the foil from damage.

20 Claims, 10 Drawing Sheets

(56) References Cited

U.S. PATENT DOCUMENTS

| | | | |
|---|---|---|---|
| 5,322,161 A * | 6/1994 | Shichman | A61B 50/30 206/204 |
| 5,392,918 A | 2/1995 | Harrison | |
| 5,415,334 A | 5/1995 | Williamson, IV et al. | |
| 5,465,895 A | 11/1995 | Knodel et al. | |
| 5,597,107 A | 1/1997 | Knodel et al. | |
| 5,632,432 A | 5/1997 | Schulze et al. | |
| 5,673,840 A | 10/1997 | Schulze et al. | |
| 5,704,534 A | 1/1998 | Huitema et al. | |
| 5,792,135 A | 8/1998 | Madhani et al. | |
| 5,814,055 A | 9/1998 | Knodel et al. | |
| 5,817,084 A | 10/1998 | Jensen | |
| 5,878,193 A | 3/1999 | Wang et al. | |
| 5,954,203 A * | 9/1999 | Marconi | B65D 81/022 206/464 |
| 6,231,565 B1 | 5/2001 | Tovey et al. | |
| 6,364,888 B1 | 4/2002 | Niemeyer et al. | |
| 6,622,864 B1 * | 9/2003 | Debbs | A61L 2/26 206/363 |
| 6,783,524 B2 | 8/2004 | Anderson et al. | |
| 6,978,921 B2 | 12/2005 | Shelton, IV et al. | |
| 6,988,650 B2 | 1/2006 | Schwemberger et al. | |
| 7,000,818 B2 | 2/2006 | Shelton, IV et al. | |
| 7,134,587 B2 | 11/2006 | Schwemberger et al. | |
| 7,143,923 B2 | 12/2006 | Shelton, IV et al. | |
| 7,147,139 B2 | 12/2006 | Schwemberger et al. | |
| 7,147,140 B2 | 12/2006 | Wukusick et al. | |
| 7,204,404 B2 | 4/2007 | Nguyen et al. | |
| 7,207,472 B2 | 4/2007 | Wukusick et al. | |
| 7,303,108 B2 | 12/2007 | Shelton, IV | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,434,715 B2 | 10/2008 | Shelton, IV et al. | |
| 7,524,320 B2 | 4/2009 | Tierney et al. | |
| 7,644,848 B2 | 1/2010 | Swayze et al. | |
| 7,691,098 B2 | 4/2010 | Wallace et al. | |
| 7,721,930 B2 | 5/2010 | McKenna et al. | |
| 7,806,891 B2 | 10/2010 | Nowlin et al. | |
| 8,096,420 B2 | 1/2012 | Marhsall et al. | |
| 8,141,762 B2 | 3/2012 | Bedi et al. | |
| 8,210,411 B2 | 7/2012 | Yates et al. | |
| 8,371,491 B2 | 2/2013 | Huitema et al. | |
| 8,408,439 B2 | 4/2013 | Huang et al. | |
| 8,453,914 B2 | 6/2013 | Laurent et al. | |
| 8,479,969 B2 | 7/2013 | Shelton, IV | |
| 8,573,461 B2 | 11/2013 | Shelton, IV et al. | |
| 8,573,465 B2 | 11/2013 | Shelton, IV | |
| 8,579,990 B2 | 11/2013 | Priewe | |
| 8,602,288 B2 | 12/2013 | Shelton, IV et al. | |
| 8,616,431 B2 | 12/2013 | Timm et al. | |
| 8,783,541 B2 | 7/2014 | Shelton, IV et al. | |
| 8,800,838 B2 | 8/2014 | Shelton, IV | |
| 8,801,735 B2 | 8/2014 | Shelton, IV et al. | |
| 8,814,025 B2 | 8/2014 | Miller et al. | |
| 8,820,605 B2 | 9/2014 | Shelton, IV | |
| 8,844,789 B2 | 9/2014 | Shelton, IV et al. | |
| 8,899,464 B2 | 12/2014 | Hueil et al. | |
| 8,992,060 B2 | 4/2015 | Dassanayake et al. | |
| 8,998,060 B2 | 4/2015 | Bruewer et al. | |
| 9,101,359 B2 | 8/2015 | Smith et al. | |
| 9,186,142 B2 | 11/2015 | Fanelli et al. | |
| 9,198,644 B2 | 12/2015 | Balek et al. | |
| 9,211,120 B2 | 12/2015 | Scheib et al. | |
| 9,301,759 B2 | 4/2016 | Spivey et al. | |
| 9,393,018 B2 | 7/2016 | Wang et al. | |
| 9,398,911 B2 | 7/2016 | Auld et al. | |
| 9,492,170 B2 | 11/2016 | Bear et al. | |
| 9,517,065 B2 | 12/2016 | Simms et al. | |
| 9,597,082 B2 | 3/2017 | Stokes et al. | |
| 9,622,746 B2 | 4/2017 | Simms et al. | |
| 9,717,497 B2 | 8/2017 | Zerkle et al. | |
| 9,795,379 B2 | 10/2017 | Leimbach et al. | |
| 9,808,248 B2 | 11/2017 | Hoffman | |
| 9,839,421 B2 | 12/2017 | Zerkle et al. | |
| 9,848,871 B2 | 12/2017 | Harris et al. | |
| 9,867,615 B2 | 1/2018 | Fanelli et al. | |
| 9,913,642 B2 | 3/2018 | Leimbach et al. | |
| 9,936,954 B2 | 4/2018 | Shelton, IV et al. | |
| 9,999,408 B2 | 6/2018 | Boudreaux et al. | |
| 10,045,780 B2 | 8/2018 | Adams et al. | |
| 10,092,292 B2 | 10/2018 | Boudreaux et al. | |
| D833,010 S | 11/2018 | Harris et al. | |
| 10,123,798 B2 | 11/2018 | Baxter, III et al. | |
| D836,198 S | 12/2018 | Harris et al. | |
| D836,199 S | 12/2018 | Schowalter et al. | |
| 10,166,023 B2 | 1/2019 | Vendely et al. | |
| 10,349,939 B2 | 7/2019 | Shelton, IV et al. | |
| 2005/0139636 A1 | 6/2005 | Schwemberger et al. | |
| 2005/0143759 A1 | 6/2005 | Kelly | |
| 2005/0145672 A1 | 7/2005 | Schwemberger et al. | |
| 2008/0169328 A1 | 7/2008 | Shelton | |
| 2012/0241493 A1 | 9/2012 | Baxter, III et al. | |
| 2013/0068816 A1 | 3/2013 | Vasudevan et al. | |
| 2013/0075447 A1 | 3/2013 | Weisenburgh et al. | |
| 2013/0206813 A1 | 8/2013 | Nalagatla | |
| 2014/0239037 A1 | 8/2014 | Boudreaux et al. | |
| 2015/0351758 A1 | 12/2015 | Shelton, IV et al. | |
| 2016/0089146 A1 | 3/2016 | Harris et al. | |
| 2016/0278774 A1 | 9/2016 | Shelton, IV et al. | |
| 2017/0027571 A1 | 2/2017 | Nalagatla et al. | |
| 2017/0049444 A1 | 2/2017 | Schellin et al. | |
| 2017/0055980 A1 | 3/2017 | Vendely et al. | |
| 2017/0055981 A1 | 3/2017 | Vendely et al. | |
| 2017/0055982 A1 | 3/2017 | Zeiner et al. | |
| 2017/0055986 A1 | 3/2017 | Harris et al. | |
| 2017/0056016 A1 | 3/2017 | Barton et al. | |
| 2017/0056017 A1 | 3/2017 | Vendely et al. | |
| 2017/0056018 A1 * | 3/2017 | Zeiner | A61B 17/105 |
| 2017/0086823 A1 | 3/2017 | Leimbach et al. | |
| 2017/0086837 A1 | 3/2017 | Vendely et al. | |
| 2017/0086842 A1 | 3/2017 | Shelton, IV et al. | |
| 2017/0290634 A1 * | 10/2017 | Dacey | A61B 50/30 |
| 2018/0235610 A1 | 8/2018 | Harris et al. | |
| 2018/0235611 A1 | 8/2018 | Harris et al. | |
| 2018/0235619 A1 | 8/2018 | Harris et al. | |
| 2019/0000481 A1 | 1/2019 | Harris et al. | |
| 2020/0205822 A1 | 7/2020 | Heupel et al. | |

OTHER PUBLICATIONS

U.S. Appl. No. 16/234,740, entitled "Surgical Stapler with Sloped Staple Deck for Varying Tissue Compression," filed Dec. 28, 2018.

U.S. Appl. No. 16/235,473, entitled "Adhesive Distribution on Buttress for Surgical Stapler," filed Dec. 28, 2018.

U.S. Appl. No. 16/235,488, entitled "Configuration of Buttress for Surgical Stapler," filed Dec. 28, 2018.

U.S. Appl. No. 16/235,503, entitled "Surgical Stapler Buttress with Tissue In-Growth Promotion," filed Dec. 28, 2018.

U.S. Appl. No. 16/235,522, entitled "Applicator for Surgical Stapler Buttress," filed Dec. 28, 2018.

U.S. Appl. No. 16/235,617, entitled "Method of Applying Buttresses to Surgically Cut and Stapled Sites," filed Dec. 28, 2018.

U.S. Appl. No. 16/235,630, entitled "Curved Tip Surgical Buttress Applicator with Opening Feature for Curved Tip Alignment," filed Dec. 28, 2018.

U.S. Appl. No. 16/235,670, entitled "Curved Tip Surgical Buttress Assembly Applicator with Proximal Alignment Features," filed Dec. 28, 2018.

U.S. Appl. No. 16/235,681, entitled "Curved Tip Surgical Buttress Assembly Applicator with Compression Layer Pocket Features," filed Dec. 28, 2018.

Design U.S. Appl. No. 29/675,045, entitled "Surgical Stapler Deck with Tissue Engagement Cleat Features," filed Dec. 28, 2018.

Design U.S. Appl. No. 29/675,047, entitled "Surgical Stapler Deck with Tissue Engagement Recess Features," filed Dec. 28, 2018.

Design U.S. Appl. No. 29/675,168, entitled "Applicator for Surgical Stapler Buttress," filed Dec. 28, 2018.

Design U.S. Appl. No. 29/675,170, entitled "Buttress for Surgical Stapler," filed Dec. 28, 2018.

(56) References Cited

OTHER PUBLICATIONS

Design U.S. Appl. No. 29/675,172, entitled "Tray for Surgical Stapler Buttress Applicator," filed Dec. 28, 2018.
Design U.S. Appl. No. 29/675,197, entitled "Applicator for a Stapler Buttress," filed Dec. 28, 2018.
Design U.S. Appl. No. 29/675,199, entitled "Buttress Assembly for a Surgical Stapler," filed Dec. 28, 2018.
U.S. Appl. No. 62/209,041, entitled "Method and Apparatus for Applying a Buttress to End Effector of a Surgical Stapler," filed Aug. 24, 2015.
European Search Report, Extended, and Written Opinion dated Mar. 26, 2020 for Application No. EP 19218546.0, 7 pgs.
International Search Report and Written Opinion dated Mar. 26, 2020 for Application No. PCT/IB2019/060546, 11 pgs.

* cited by examiner

PACKAGING FOR SURGICAL STAPLER BUTTRESS

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. patents is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited for use through a thoracotomy are disclosed in U.S. Pat. No. 9,186,142, entitled "Surgical Instrument End Effector Articulation Drive with Pinion and Opposing Racks," issued Nov. 17, 2015; U.S. Pat. No. 9,717,497, entitled "Lockout Feature for Movable Cutting Member of Surgical Instrument," issued Aug. 1, 2017; U.S. Pat. No. 9,517,065, entitled "Integrated Tissue Positioning and Jaw Alignment Features for Surgical Stapler," issued Dec. 13, 2016; U.S. Pat. No. 9,839,421, entitled "Jaw Closure Feature for End Effector of Surgical Instrument," issued Dec. 12, 2017; U.S. Pat. No. 9,867,615, entitled "Surgical Instrument with Articulation Lock having a Detenting Binary Spring," issued Jan. 16, 2018; U.S. Pat. No. 9,622,746, entitled "Distal Tip Features for End Effector of Surgical Instrument," issued Apr. 18, 2017; U.S. Pat. No. 10,092,292, entitled "Staple Forming Features for Surgical Stapling Instrument," issued Oct. 9, 2018; U.S. Pat. No. 9,795,379, entitled "Surgical Instrument with Multi-Diameter Shaft," issued Oct. 24, 2017; and U.S. Pat. No. 9,808,248, entitled "Installation Features for Surgical Instrument End Effector Cartridge," issued Nov. 7, 2017. The disclosure of each of the above-cited U.S. Patent Publications is incorporated by reference herein.

Additional surgical stapling instruments are disclosed in U.S. Pat. No. 8,801,735, entitled "Surgical Circular Stapler with Tissue Retention Arrangements," issued Aug. 12, 2014; U.S. Pat. No. 8,141,762, entitled "Surgical Stapler Comprising a Staple Pocket," issued Mar. 27, 2012; U.S. Pat. No. 8,371,491, entitled "Surgical End Effector Having Buttress Retention Features," issued Feb. 12, 2013; U.S. Pat. No. 9,597,082, entitled "Method and Apparatus for Sealing End-to-End Anastomosis" issued Mar. 21, 2017; U.S. Pat. No. 9,398,911, entitled "Rotary Powered Surgical Instruments with Multiple Degrees of Freedom," issued Jul. 26, 2016; U.S. Pub. No. 2013/0206813, entitled "Linear Stapler," published Aug. 15, 2013; U.S. Pub. No. 2008/0169328, entitled "Buttress Material for Use with a Surgical Stapler," published Jul. 17, 2008; U.S. Pat. No. 9,848,871, entitled "Woven and Fibrous Materials for Reinforcing a Staple Line," issued Dec. 26, 2017; U.S. Pat. No. 9,936,954, entitled "Devices and Methods for Sealing Staples in Tissue" issued Apr. 10, 2018; and U.S. Pat. Pub. No. 2016/0089146, entitled "Radically Expandable Staple Line" published Mar. 31, 2016. The disclosure of each of the above-cited U.S. patents, U.S. Patent Publications, and U.S. patent applications is incorporated by reference herein.

In some instances, it may be desirable to equip a surgical stapling instrument with a buttress material to reinforce the mechanical fastening of tissue provided by staples. Such a buttress may prevent the applied staples from pulling through tissue and may otherwise reduce a risk of tissue tearing at or near the site of applied staples. When using a buttress material to reinforce a cut and stapled tissue site, a buttress applicator may be used to load one or more buttresses onto the end effector for subsequent deployment at the cut and stapled tissue site. To preserve the integrity of the buttresses prior to loading and deployment of buttresses at a tissue site, various packaging is used for the buttresses and/or applicators containing the buttresses.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
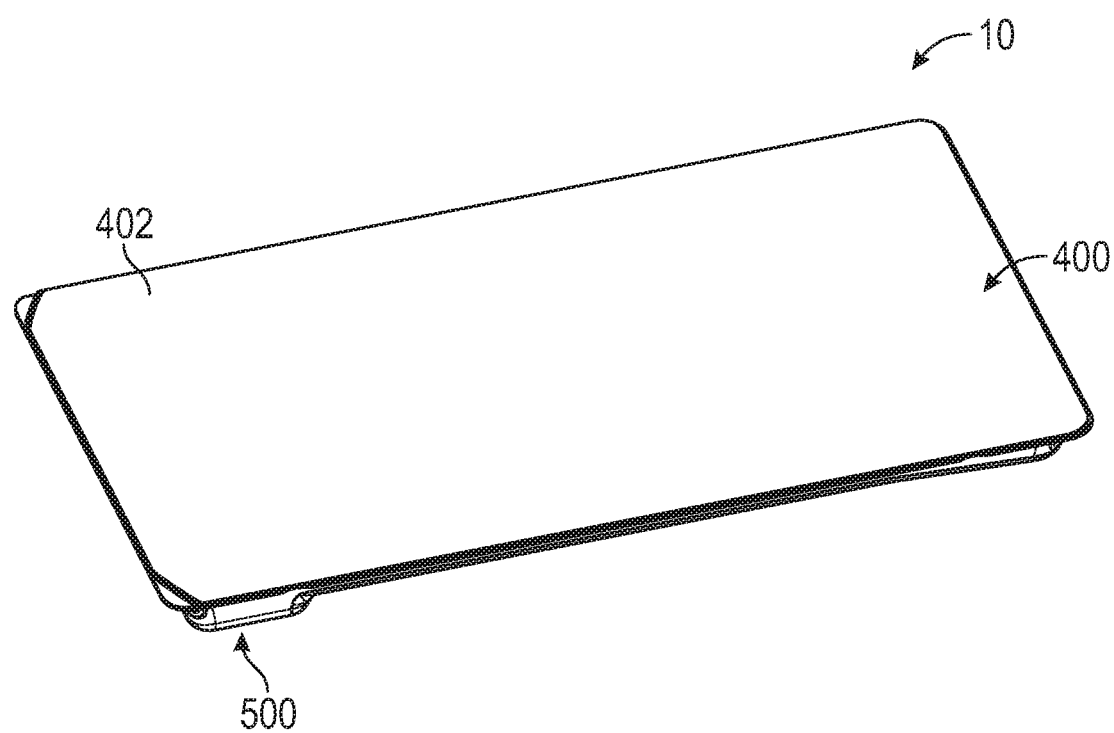
FIG. 1 depicts a top perspective view of an exemplary packaging assembly for an applicator having a buttress assembly for use with a surgical stapler.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. EXEMPLARY PACKAGING ASSEMBLY FOR BUTTRESS APPLICATOR

As mentioned above, it can be beneficial to apply a buttress to a cut and stapled surgical site as a reinforcement. In doing so, the buttress must be loaded onto an end effector of a surgical stapler, and then applied at the site releasing from the end effector in the process. In use the buttress can be configured to be bioabsorbable so over time it is completely absorbed by the body of the patient. To achieve the desired loading and release properties of the buttress, as well as desired reinforcement properties when in use, the buttress material itself, as well as materials applied to the buttress such as adhesive, can be susceptible to degradation when exposed prematurely to environmental factors such as moisture, etc. Using a packaging assembly as shown and described herein can preserve the integrity of the buttress prior to its use and application.

A. Exemplary Outer Tray and Foil Assembly

Figure 5:
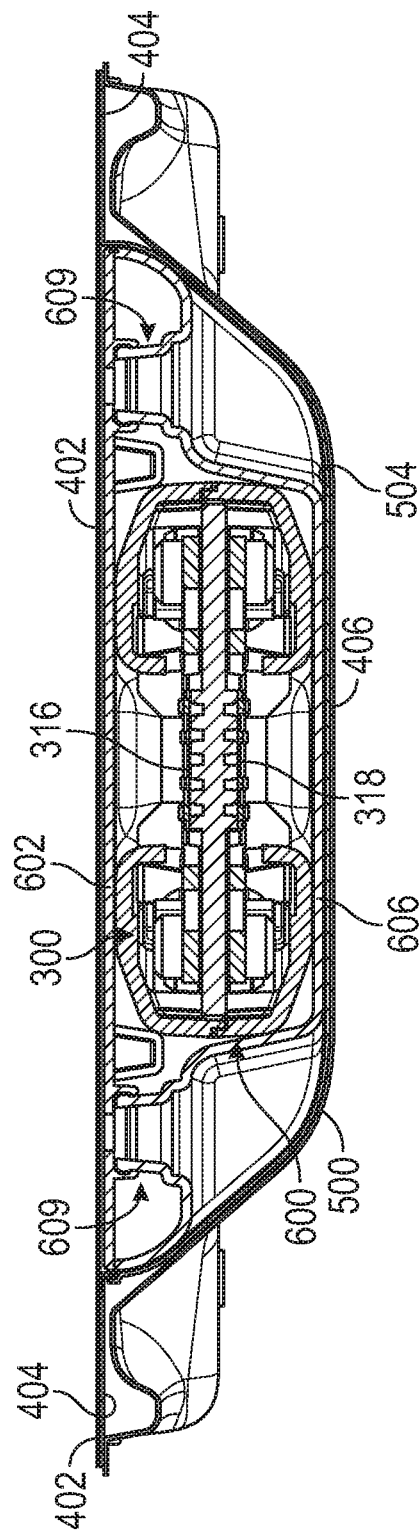
FIG. 5 depicts a cross-section view of the packaging assembly of FIG. 3, taken along line 5-5 of FIG. 3.
Figure 6:
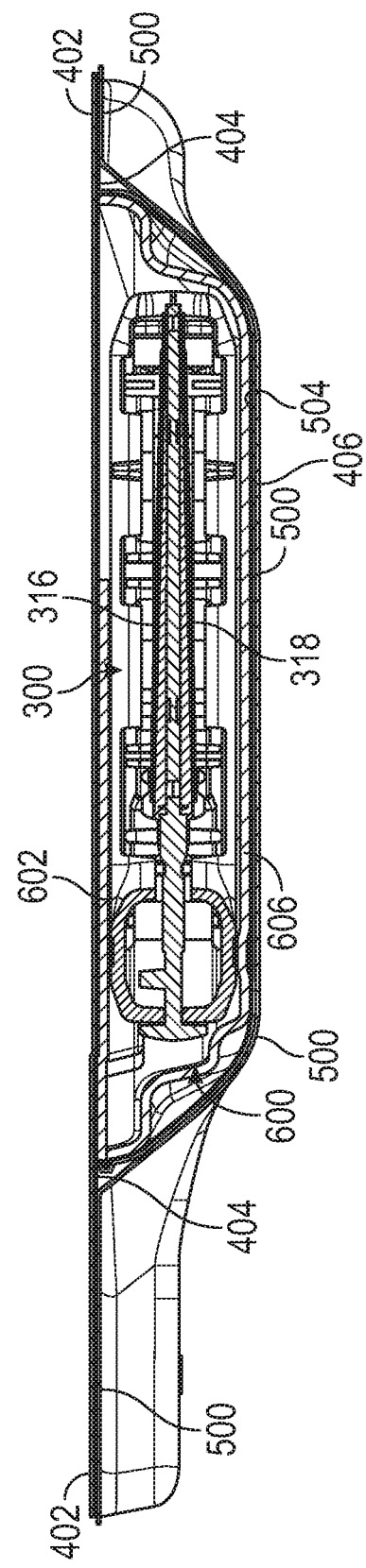
FIG. 6 depicts a cross-section view of the packaging assembly of FIG. 4, taken along line 6-6 of FIG. 4.
Figure 8:
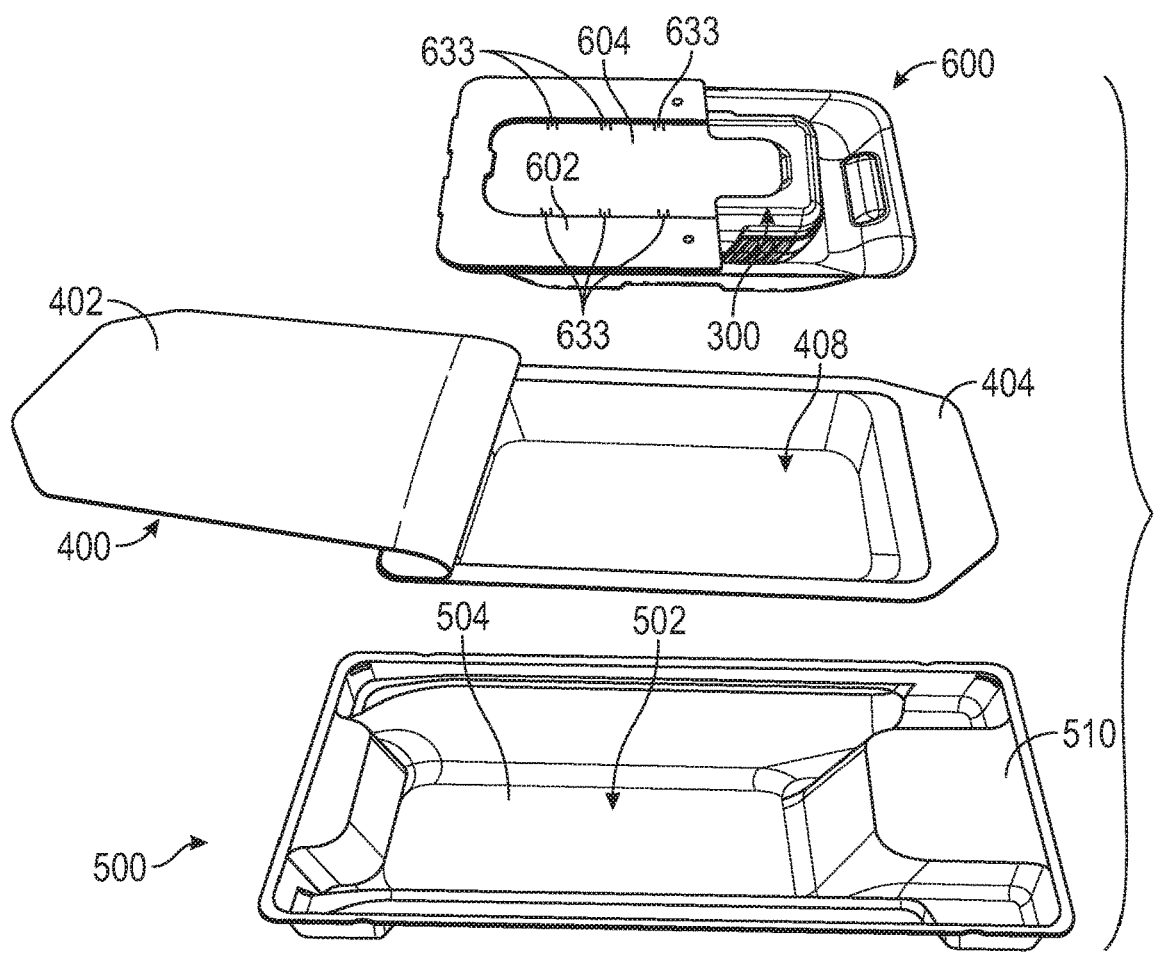
FIG. 8 depicts a partial exploded view of the packaging assembly of FIG. 1, shown with the outer tray, foil assembly, and inner tray with applicator separate one another, and with the flap of the inner tray in a closed position.

FIGS. 1-6 illustrate an exemplary packaging assembly (10) for a buttress applicator of a surgical stapler. Packaging assembly comprises a foil assembly or foil pouch (400) and an outer tray (500). Foil pouch (400) comprises a top layer (402) as shown in FIG. 1, and a bottom layer (404) as shown in FIGS. 5-6. Outer tray (500) is positioned such that foil pouch (400) sits within outer tray (500). In this respect, outer tray (500) comprises a cavity or space (502), as shown in FIG. 8, configured to received foil pouch (400). At least a portion of outer tray (500) has a shape that matches or closely matches a shape of an underside (406) of foil pouch (400) as best seen in FIGS. 5 and 6. In this manner in the present example, a surface (504) of cavity (502) is immediately adjacent to underside (406) of foil pouch (400). With this configuration, outer tray (500) is configured to protect bottom layer (404) of foil pouch (400) from damage by fitting closely against bottom layer (404).

Figure 2:
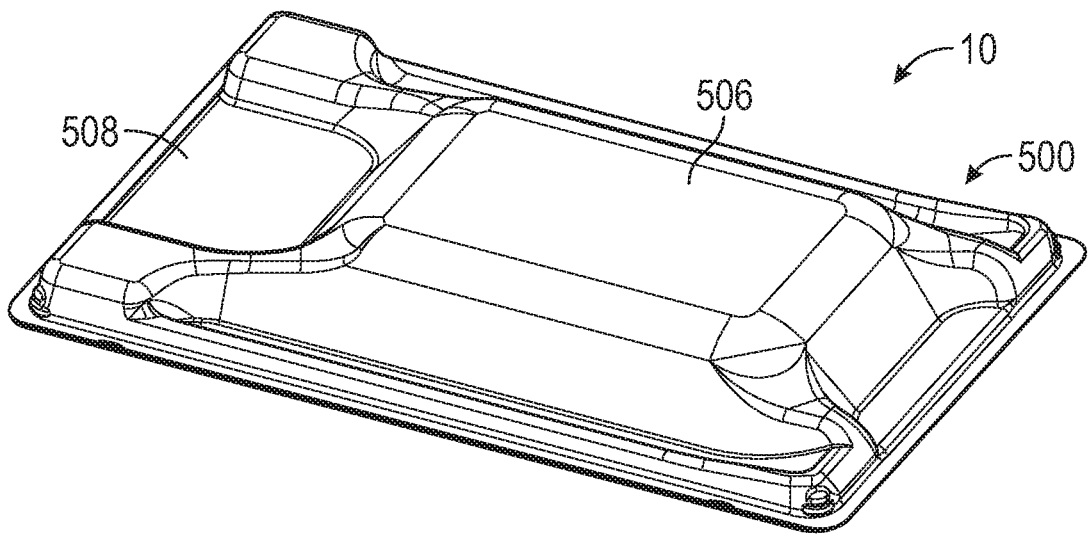
FIG. 2 depicts a bottom perspective view of the packaging assembly of FIG. 1.
Figure 3:
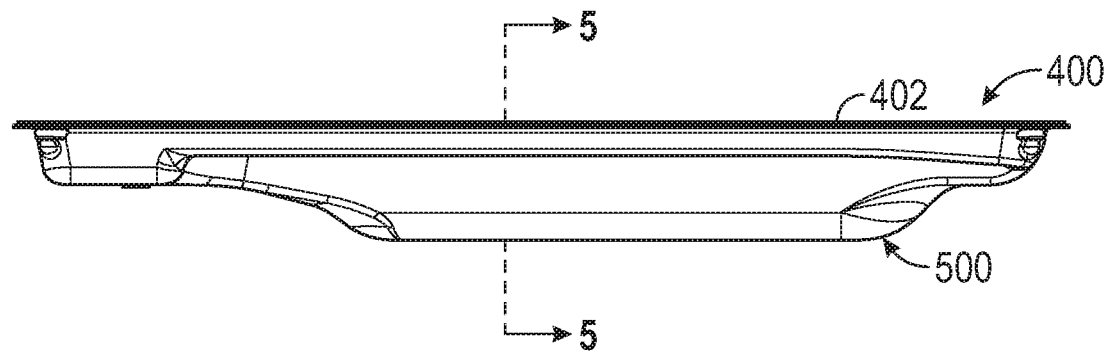
FIG. 3 depicts a side view of the packaging assembly of FIG. 1, taken along the long side of the packaging assembly.
Figure 4:
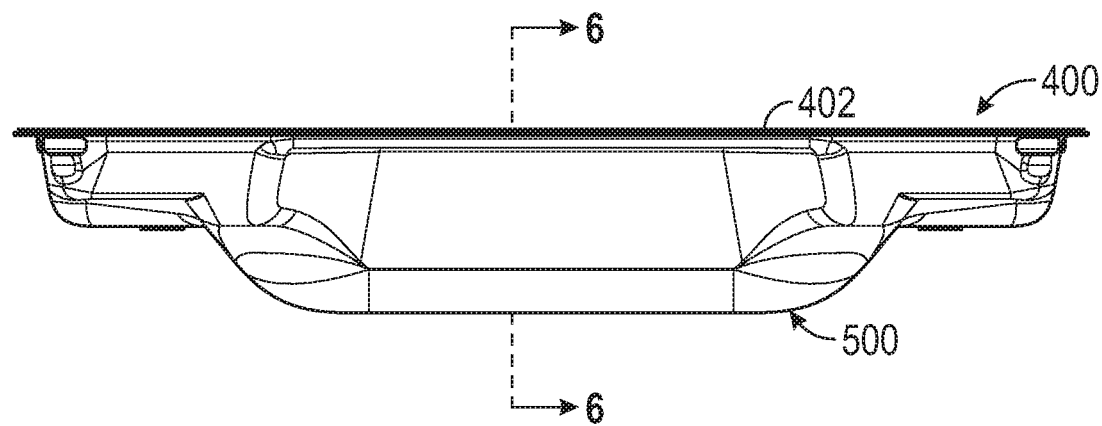
FIG. 4 depicts a side view of the packaging assembly of FIG. 1, taken along the short side of the packaging assembly.

Referring to FIG. 2, outer tray (500) is configured for stacking with outer tray (500) comprising a smooth flat underside (506). The smooth and flat nature of underside (506) allows for stacking multiple packaging assemblies (10) on top of one another, without underside surface (506) damaging top layer (402) of an adjacent foil pouch (400). The size and shape of underside (506) is configured such that a flap (602) of an inner tray (600)—as shown in FIGS. 5 and 6—of one packaging assembly (10) can provide structural support to bear the weight of another packaging assembly (10) stacked thereupon. In this manner, top layer (402) of foil pouch (400) is not required in all cases to bear the weight or load of whatever packaging assemblies (10) are stacked above, which preserves the integrity of foil pouch (400) by preventing creasing or puncture of top layers (402) of stacked packaging assemblies (10).

Still referring to FIG. 2, outer tray (500) also comprises recess (508) on a bottom side. Recess (508) is configured as an area that can be easily accessed and grasped by a user to pick up a select packaging assembly (10) either separately or from a group of stacked packaging assemblies (10). With this configuration, opposite recess (508) on a top side of outer tray (500) is a flat surface (510) as shown in FIG. 8, which is configured as a complementary area that can be easily accessed and grasped by a user to pick up a select packaging assembly (10) either separately or from a group of stacked packaging assemblies (10). In this manner, outer tray (500) is configured with an accessible area for a user to grasp, hold, or pick up packaging assembly (10) easily and safely without risk of contacting buttress and/or buttress applicator.

B. Exemplary Foil Assembly and Inner Tray

Figure 7:
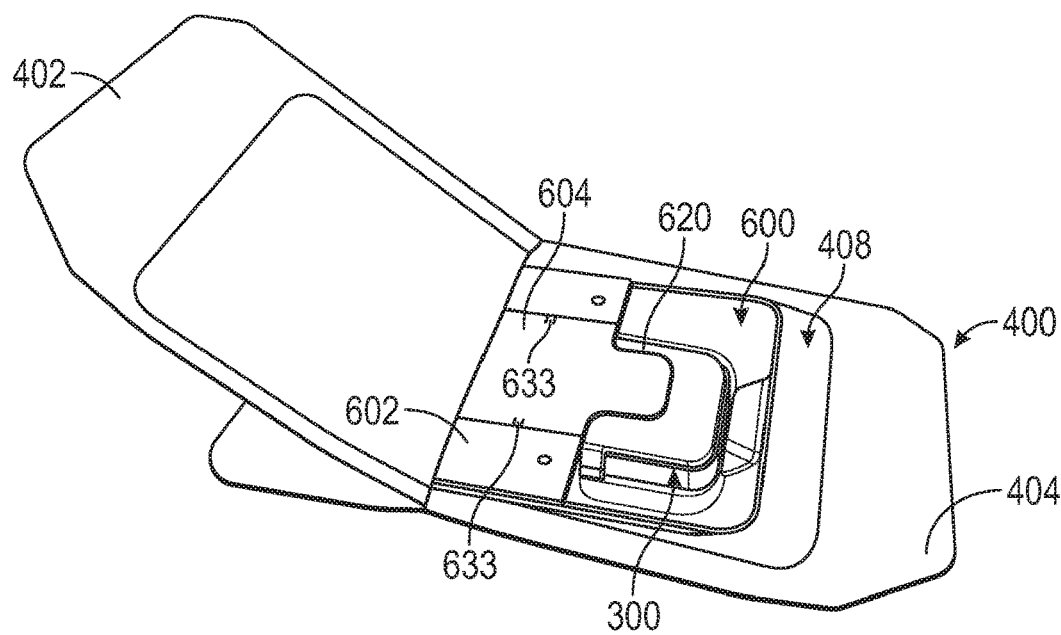
FIG. 7 depicts a top perspective view of the packaging assembly of FIG. 1, shown without the outer tray and with the foil assembly partially opened.

FIG. 7 illustrates a portion of packaging assembly (10), where outer tray (500) has been set aside. Furthermore, foil pouch (400) is shown as partially opened, with top layer (402) peeled back and away from bottom layer (404). As shown, foil pouch (400) comprises an interior (408) between top and bottom layers (402, 404). Furthermore, interior (408) is configured to receive, retain, or hold inner tray (600), which receives, retains, or holds a buttress applicator (300). Prior to top layer (402) and bottom layer (404) being separated, top layer (402) and bottom layer (404) are connectable to seal inner tray (600) with buttress applicator (300) within foil pouch (400). In the present example, top and bottom layers (402, 404) seal together to form a hermetic seal. In this way, the seal is airtight such that moisture outside foil pouch (400) cannot enter and thereby damage or degrade the buttress assemblies (316, 318) of buttress applicator (300). As noted and shown, the hermetic seal between top layer (402) and bottom layer (404) is selective and not permanent such that a user can separate top and bottom layers (402, 404) to retrieve buttress applicator (300). In some examples, foil pouch (400) is sealed under dry nitrogen to provide interior (408) with an extremely low moisture and oxygen environment.

With foil pouch (400) sealed and surrounding inner tray (600), top layer (402) of foil pouch (400) and bottom layer (404) of foil pouch (400) are configured to closely follow the contour of inner tray (600). This close fit, which can be seen in the cross-section views of FIGS. 5 and 6, promotes protection of foil pouch (400) from damage when and if being contacted, as inner tray (600) provides support to top and bottom layers (402, 404) of foil pouch (600) from the inside of foil pouch (400) outward. By way of example only, if too much space is provided between foil pouch (400) and inner tray (600) when inner tray (600) is sealed within foil pouch (400), then top and/or bottom layers (402, 404) of foil pouch (400) are more susceptible to damage in the form of creases, cuts, and/or punctures.

With the configuration described above, packaging assembly (10) is configured with two trays: inner tray (600) and outer tray (500). Moreover, inner tray (600) and outer tray (500) are separable from one another. In the present example, foil pouch (400) separates inner tray (600) from outer tray (500), and more specifically, bottom layer (404) of foil pouch (400) separates inner tray (600) from outer tray (500). Foil pouch (400) is configured as an impermeable material such that water and air cannot pass through layers (402, 404) of foil pouch (400). Thus, in one version packaging assembly (10) comprises outer tray (500) and inner tray (600) configured to selectively retain buttress applicator (300), where there is an impermeable material positionable between outer tray (500) and inner tray (600). Furthermore, the impermeable material surrounds buttress applicator (300) retained by inner tray (600) forming a hermetic seal around inner tray (600) and buttress applicator (300). Further yet, with the above-described configuration, outer tray (500) is configured to protect the impermeable material from damage. While the present example shows packaging assembly (10) with two trays (600, 500) separable by impermeable bottom foil layer (404), in other versions, packaging assembly (10) can be configured with greater or fewer trays and separable by other materials as will be appreciated by those of ordinary skill in the art in view of the teachings herein.

While examples of packaging assembly (10) herein describe pouch (400) as foil pouch (400), it should be understood that pouch (400) is not limited to being constructed of foil. In other examples, pouch (400) is constructed of other suitable materials that can provide a hermetic seal. Such other suitable materials can include impermeable films such as films made of various plastics. In view of the teachings herein, other materials for use in constructing pouch (400) of packaging assembly (10) will be apparent to those of ordinary skill in the art.

C. Exemplary Inner Tray and Buttress Applicator

Figure 9:
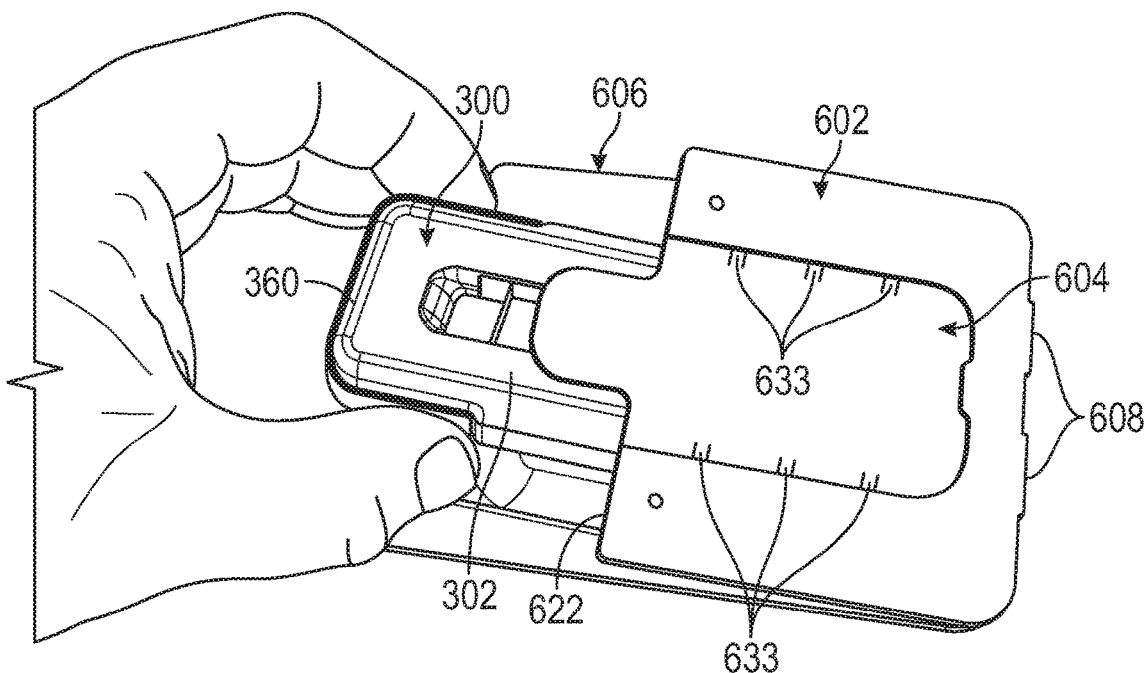
FIG. 9 depicts a top perspective view of the inner tray and applicator of FIG. 7, with the applicator partially lifted from the inner tray and the flap of the inner tray partially lifted.
Figure 10:
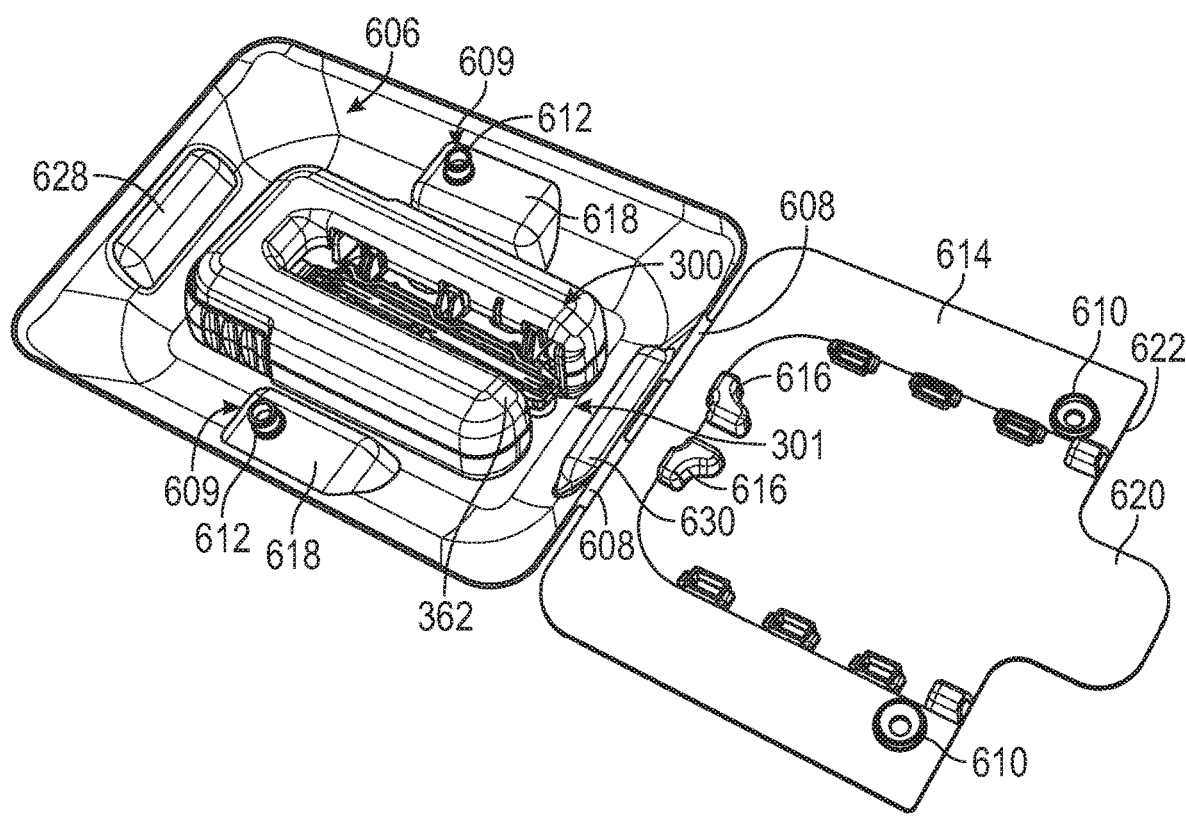
FIG. 10 depicts a top perspective view of the inner tray and applicator of FIG. 7, shown with the flap of the inner tray in an open position.
Figure 11:
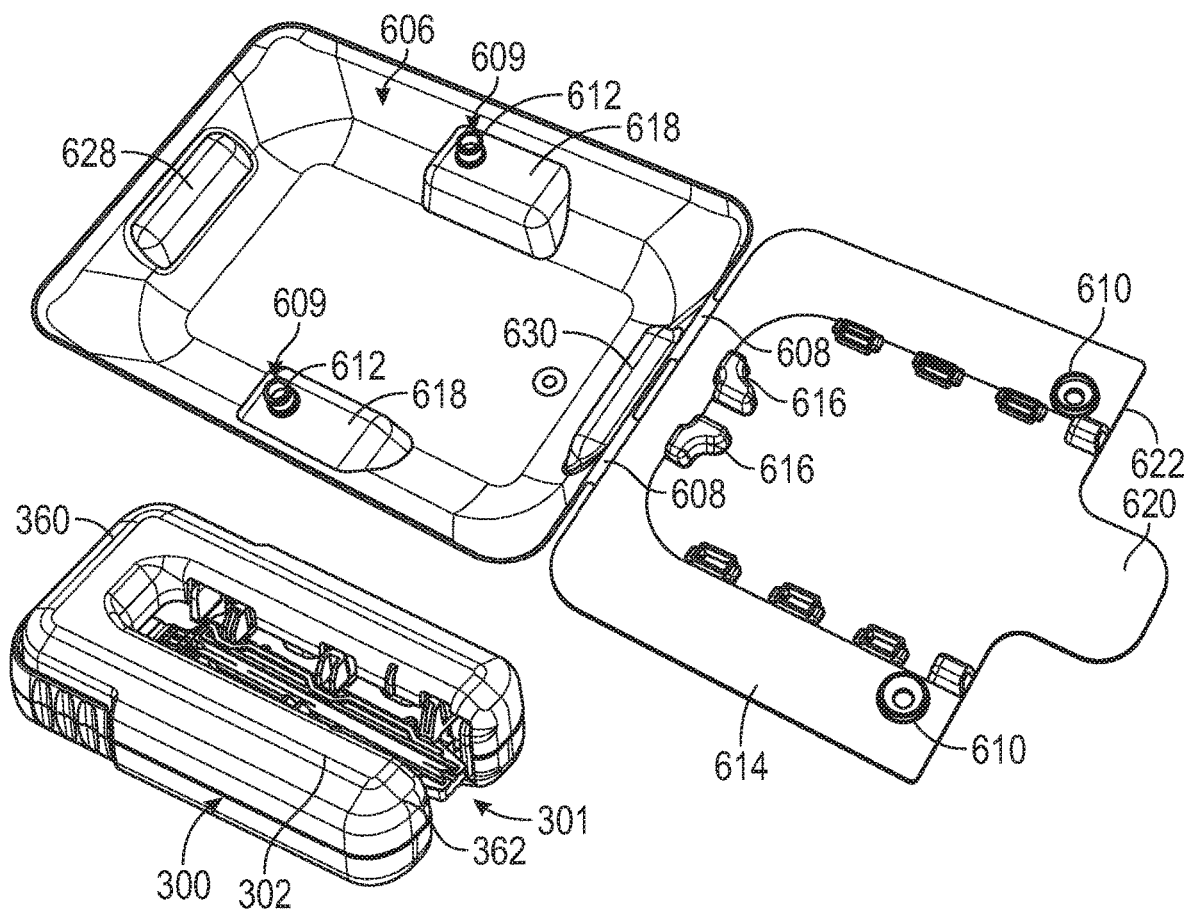
FIG. 11 depicts a top perspective view of the inner tray and applicator of FIG. 7, shown with the applicator removed from the inner tray.

FIGS. 9-11 illustrate inner tray (600), including buttress applicator (300). In some instances buttress applicator (300) is referred to herein as merely applicator (300). It should be understood that these terms are used and understood herein to be interchangeable. As illustrated, inner tray (600) comprises a base (606), flap (602), and a living hinge (608) connecting flap (602) with base (606). Base (606) of inner tray (600) is configured to selectively retain applicator (300). Flap (602) is rotatable from a closed position as seen in FIGS. 7-9, to an open position as seen in FIGS. 10 and 11. In the closed position, flap (602) at least partially covers applicator (300) when applicator (300) is retained within base (606). In the open position, flap (602) reveals applicator (300) such that it may be removed from inner tray (600).

Figure 13:
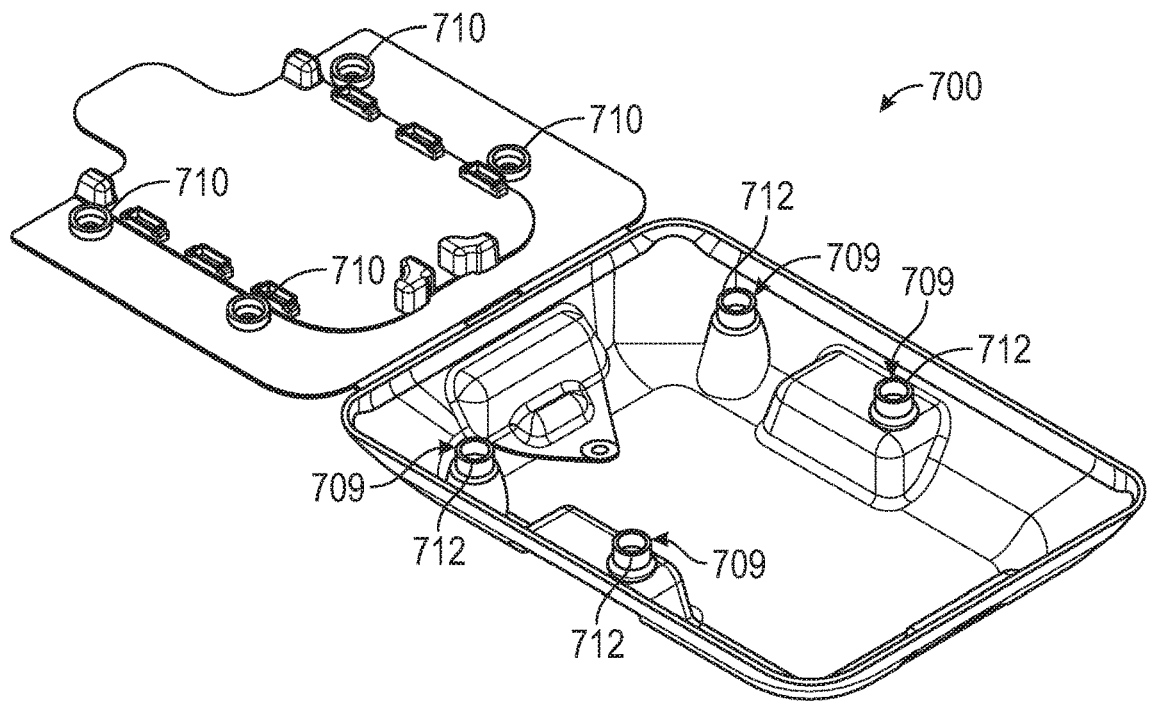
FIG. 13 depicts a top perspective view of another exemplary inner tray configured for use with the packaging assembly of FIG. 1.
Figure 14:
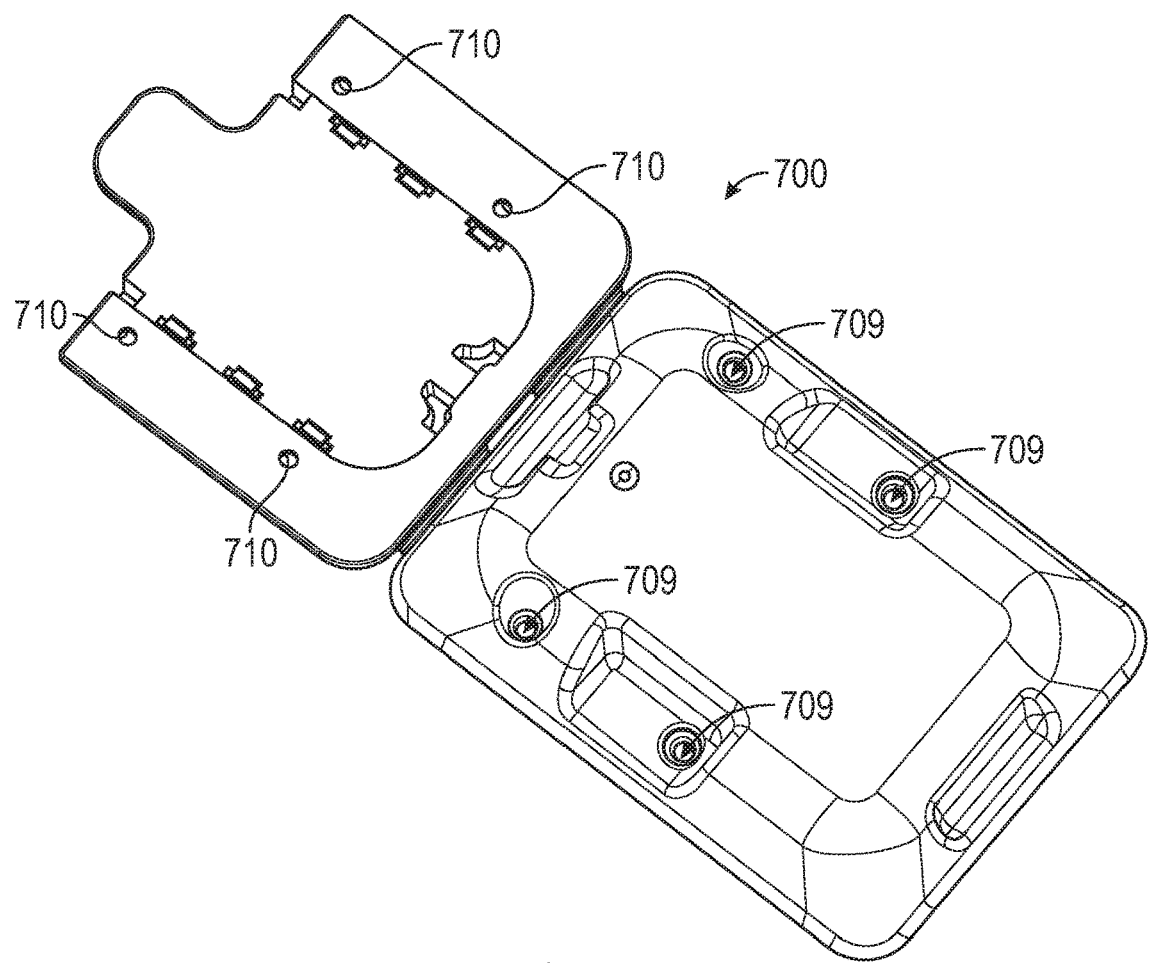
FIG. 14 depicts a bottom perspective view of the inner tray of FIG. 13.

Inner tray (600) includes fastening features (609) that are configured to selectively engage so that flap (602) connects with base (606) as mentioned above. In the present example, one fastening feature (609) comprises fastening members (610, 612), with one fastening member (610) located on an underside (614) of flap (602), and the other fastening member (612) located on a ridge (618) within base (606). Fastening members (610) engage with fastening members (612) when flap (602) is in the closed position. While the illustrated version of FIGS. 9-11 shows a pair of fastening features (609), in other versions greater or fewer fastening features (609)—and their associated fastening members (610, 612)—may be used to achieve selective closure of flap (602) with body (606). By way of example only, and not limitation, FIGS. 13 and 14 illustrate another exemplary inner tray (700). Inner tray (700) is the same as inner tray (600) with the exception that inner tray (700) comprises two pair, or four total, fastening features (709), each with fastening members (710) that are configured to selectively engage with fastening members (712).

Returning to FIGS. 9 and 10, in some versions, inner tray (600) is configured such that applicator (300) only sits within base (606) and with flap (602) closable when applicator (300) is oriented or positioned in a certain manner. For instance, as shown in FIG. 9, inner tray (600) presents a distal end (360) of applicator (300) for a user to grasp. Proximal end (362) of applicator (300) is covered by flap (602) when flap (602) is closed. Flap (602) is configured with guide features (616) along its underside (614), where guide features (616) are configured to locate within a space created by an open end (301) of applicator (300). Because applicator (300) is a closed structure along its distal end (360), if applicator (300) is positioned within base (606) with its proximal end (362) presenting towards a user for grasping—opposite of what is shown in FIG. 9—then guide features (616) will interfere with the closed distal end (360) of applicator (300) such that flap (602) cannot close fully with fastening members (610) engaging fastening members (612).

In this configuration, a poka-yoke relationship or configuration exists among inner tray (600) and applicator (300) to ensure applicator (300) is oriented with its distal end (360) visible and its proximal end (362) covered by flap (602) when flap (602) is closed. This orientation of applicator (300) relative to inner tray (600) provides that flap (602) shields buttress assemblies (316, 318) of applicator (300) so that buttress assemblies (316, 318) are inaccessible. In this manner, flap (602) protects buttress assemblies (316, 318) from contact when applicator (300) is positioned within inner tray (600) with flap (602) closed. Additionally, base (606) of inner tray (600) further includes ridges (618) and stops (628, 630) as shown in FIGS. 10 and 11 that help minimize applicator (300) shifting or moving when seated within base (606) of tray (600). For instance, ridges (618) help minimize lateral movement of applicator (300), while stops (628, 630) help minimize longitudinal movement of applicator (300).

Referring to FIG. 9, inner tray (600) and applicator (300) are configured in the present example such that flap (602) can be disengaged from base (606) by lifting distal end (360) of applicator (300). In this way, housing portion (302) of applicator (300) pushes on underside (614) of flap (602) to release the engagement between fastening members (610, 612). This opening technique helps prevent or shield buttress assemblies (316, 318) from contact. Still other ways to open flap (602) exist. For example, flap (602) comprises peninsula portion (620). Portion (620) may be grasped by a user and lifted to open flap (602) for removal of applicator (300). Peninsula portion (620) further allows for a center region of applicator (300) having buttress assemblies (316, 318) to be covered when flap (602) is closed, while exposing distal end (360) of applicator (300) for visualization or grasping by a user. Still further, flap (602) presents a leading edge (622), which can be contacted by a user and lifted to move flap (602) from its closed position to its open position. In view of the teachings herein, other ways to facilitate opening flap (602) to remove applicator (300) from inner tray (600) while protecting buttress assemblies (316, 318) from contact and other environmental exposure will be apparent to those of ordinary skill in the art.

D. Exemplary Inner Tray and Desiccant Material

Figure 12:
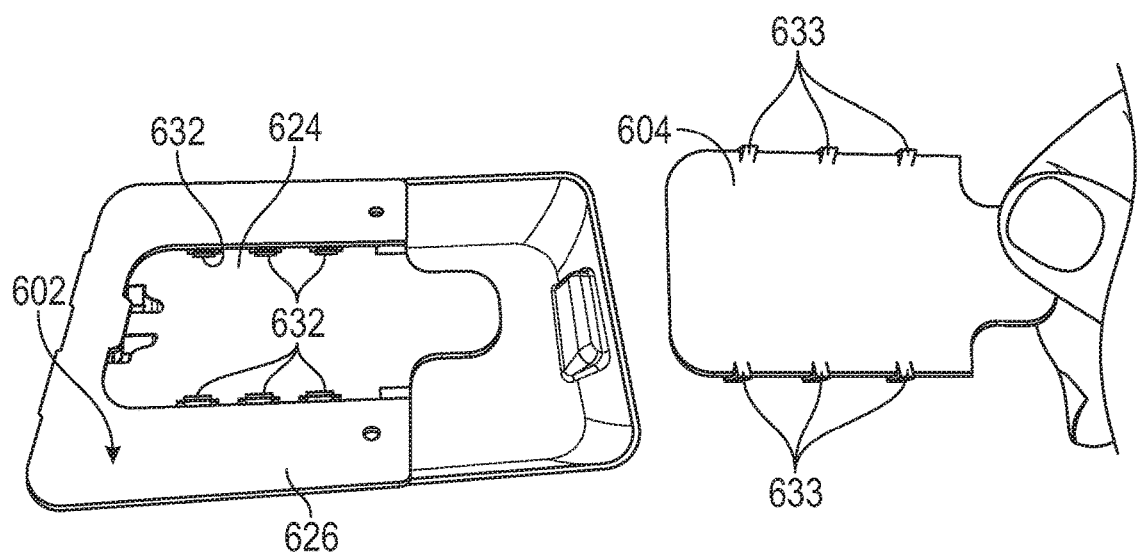
FIG. 12 depicts a top perspective view of the inner tray of FIG. 7, shown with the desiccant material removed from the inner tray.

As shown in FIGS. 9 and 12, inner tray (600) is configured to selectively retain a desiccant material (604). Desiccant material (604) is configured to preferentially absorb any moisture within interior (408) of foil pouch (400). In this way, desiccant material (604) may be an overdried material that is combined with inner tray (600) and then sealed within foil pouch (400). Any moisture that exists within foil pouch (400) will be first absorbed by the overdried desiccant material (604) before being absorbed by buttress assemblies (316, 318) of buttress applicator (300). In the present example, desiccant material (604) comprises a piece of paperboard, but in other versions desiccant material (604) can be made of other materials such as cotton, silica, and other materials that will be apparent to those of ordinary skill in the art in view of the teachings herein.

Referring to FIG. 12, inner tray (600) comprises an area (624) on an outer surface (626) of flap (602) that is configured to selectively retain desiccant material (604). In this configuration, inner tray (600) selective retains desiccant material (604) in a way where desiccant material (604) does not contact applicator (300). In one example, area (624) of flap (602) comprises tabs. In the present example, inner tray (600) comprises a molded plastic and accordingly area (624) and tabs are molded features of inner tray (600). Desiccant material (604) and tabs are configured such that desiccant material (604) can be slid along area (624) with tabs sliding above desiccant material (604) to selectively retain desiccant material (604) adjacent to area (624) of flap (602). Similarly, desiccant material (604) can be removed from inner tray (600) by sliding desiccant material (604) distally away from area (624) such that tabs no longer impinge on and retain desiccant material (604) with inner tray (600). Referring to FIG. 12, in another example, area (624) of flap (602) comprises openings (632). In the present example, inner tray (600) comprises a molded plastic and accordingly area (624) and openings (632) are molded features of inner tray (600). Furthermore, desiccant material (604) comprises tabs (633), which are engagement features that can be inserted into and received by openings (632) such that desiccant material (604) can be selectively attached with area (624). In the present example, tabs (633) are resiliently biased outward from a longitudinal centerline of desiccant material (604). When inserted within openings (632) tabs (633) deflect inward and the resilient bias of tabs (633) provide a selective interference fitting between tabs (633) and openings (632) to selectively retain desiccant material (604) with area (624) of flap (602). Desiccant material (604) can be removed from inner tray (600) by pulling desiccant material (604) upward away from area (624) of flap (602) to overcome the interference fitting such that tabs (633) disengage from openings (632). In view of the teachings herein, other ways to attach and remove desiccant material (604) with inner tray (600) will be apparent to those of ordinary skill in the art.

II. EXEMPLARY BUTTRESS APPLICATOR

Figure 15:
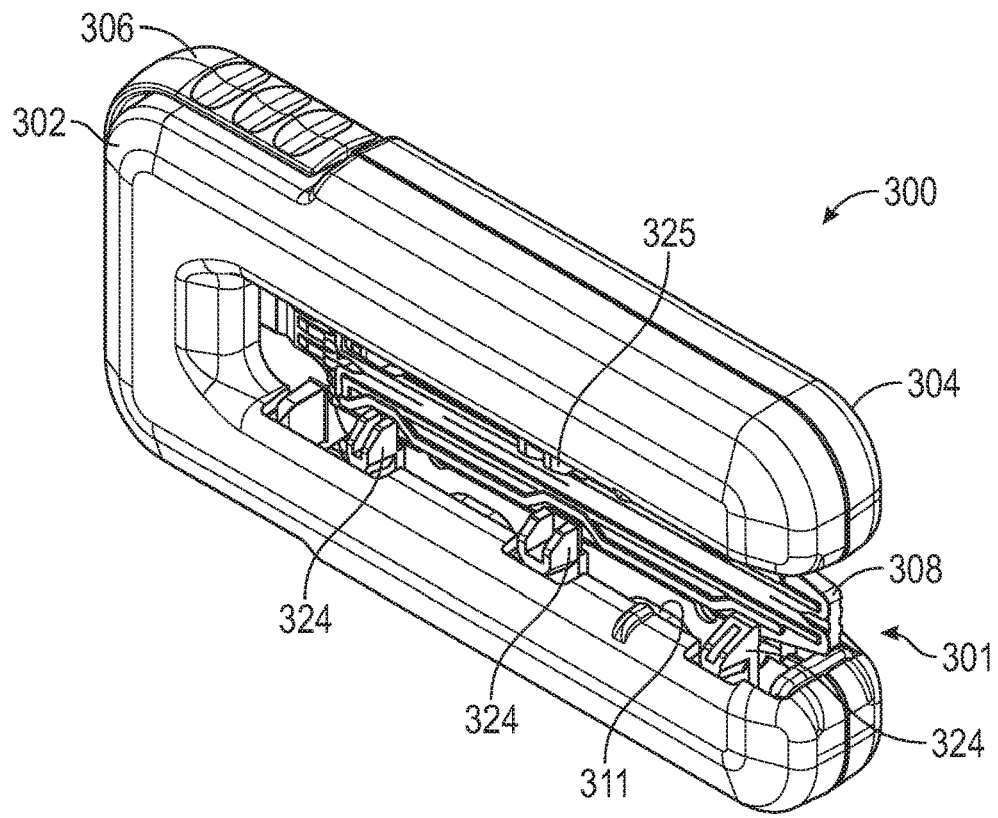
FIG. 15 depicts a perspective view of the buttress applicator of FIG. 7.
Figure 16:
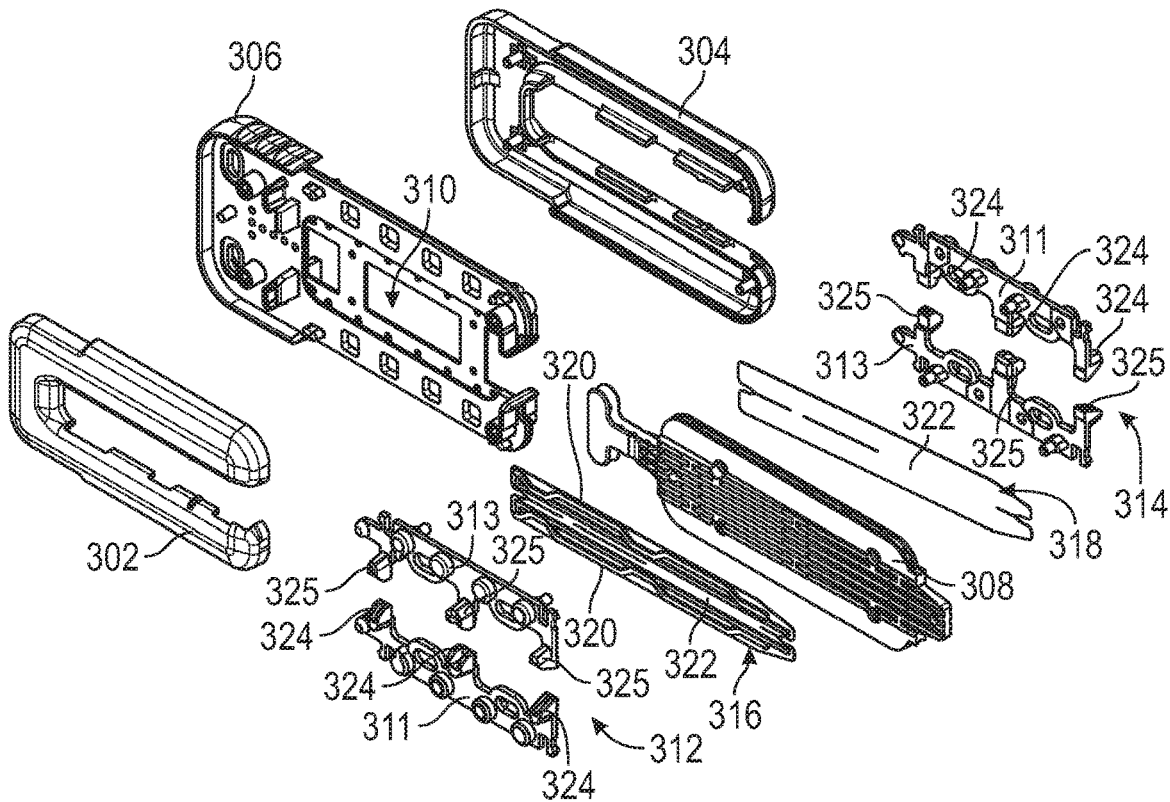
FIG. 16 depicts an exploded view of the buttress applicator of FIG. 15.

FIGS. 15 and 16 illustrate buttress applicator (300) for use with an end effector, for example end effector (40) described below with reference to FIGS. 17 and 18. Buttress applicator (300) comprises a first housing portion (302) and a second housing portion (304). Each of housing portions (302, 304) connects with a frame (306). A compression pad (308) is configured to fit within a central portion (310) of frame (306). A first pair of clamp arms (312) are located on a first side of frame (306) between frame (306) and housing portion (302). A second pair of clamp arms (314) are located on a second side of frame (306) between frame (306) and housing portion (304). In the present version, clamp arms (312) comprise a left clamp arm (311) and a right clamp arm (313). Similarly, clamp arms (314) comprise a left clamp arm (311) and a right clamp arm (313). Buttress assemblies (316, 318) are located on respective sides of compression pad (308), and when buttress applicator (300) is fully assembled, pairs of clamp arms (312, 314) selectively retain buttress assemblies (316, 318) against compression pad (308). In the present example buttress assemblies (316, 318) are the same with each comprising an adhesive (320) located on a buttress (322) as will be described in greater detail below.

Buttress applicator (300) can be used with end effector (40) in the same manner as described below with respect to buttress applicator (200). For instance, buttress assemblies (316, 318) are loaded to end effector (40) in the same manner as described below where end effector (40) is moved to a closed or clamped position once anvil (60) and lower jaw (50) are positioned over central portion (310) of frame (306). More specifically, the clamping action of end effector (40) when over buttress assemblies (316, 318) and compression pad (308) causes anvil (60) and staple cartridge (70) of lower jaw (50) to contact retention features (324) on left clamp arms (311) and retention features (325) on right clamp arms (313). This contact drives clamp arms (311, 313) laterally away from buttress assemblies (316, 318) thereby disengaging retention features (324, 325) from buttress assemblies (316, 318). With retention features (324, 325) disengaged, depending on the clamping orientation used with end effector (40), adhesive (320) of buttress assembly (316) contacts either underside (65) of anvil (60) or deck (73) of staple cartridge (70), while adhesive (320) of buttress assembly (318) contacts the other of underside (65) of anvil (60) or deck (73) of staple cartridge (70). This causes buttress assemblies (316, 318) to attach with end effector (40) and remain with end effector (40) as end effector is opened and moved away from buttress applicator (300). From this point, buttress assemblies (316, 318) may be applied to a cut and stapled tissue site.

III. EXEMPLARY BUTTRESS LOADING AND APPLICATION

Figure 17:
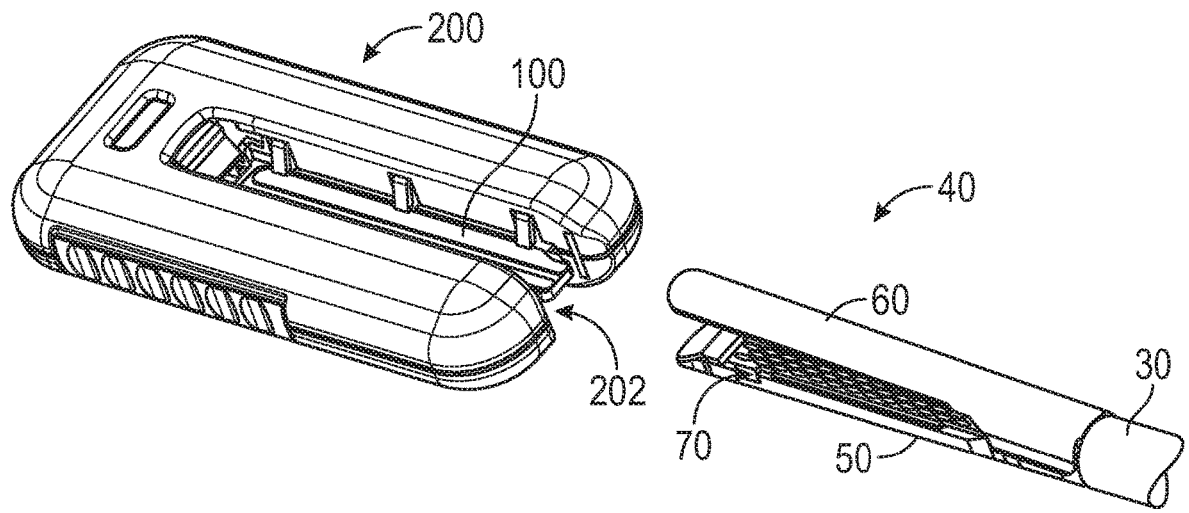
FIG. 17 depicts a perspective view of an exemplary end effector of a surgical stapler and another exemplary buttress applicator usable with the packaging assembly of FIG. 1, with the end effector approaching the buttress applicator.
Figure 18:
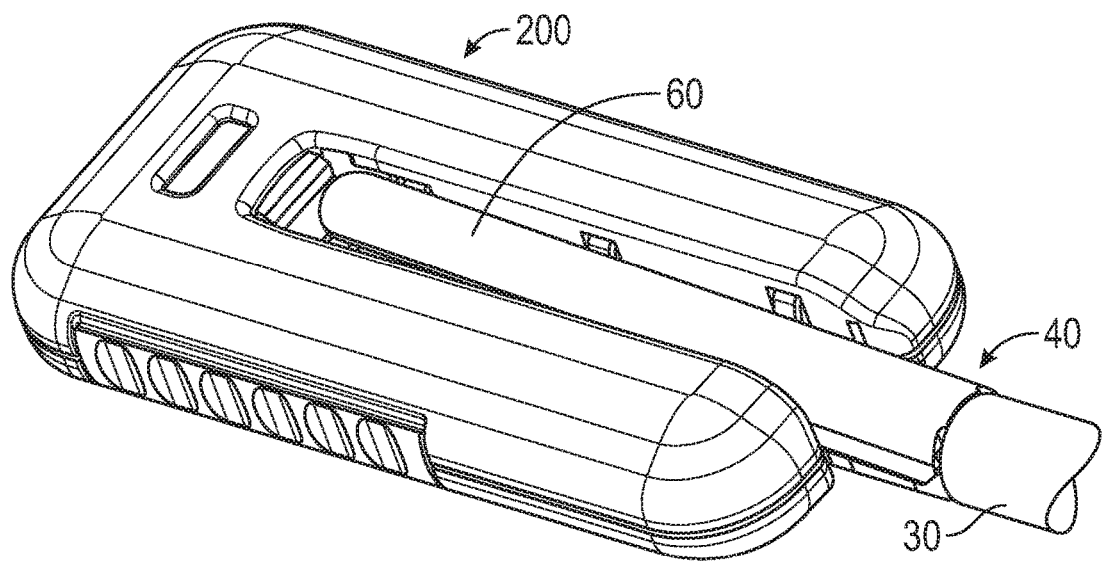
FIG. 18 depicts a perspective view of the end effector and the buttress applicator of FIG. 17, with the buttress applicator positioned in the end effector.

FIGS. 17 and 18 illustrate an exemplary end effector (40) configured to apply a buttress to a tissue site where a cutting and stapling operation is performed. End effector (40) is connected with a shaft assembly (30). End effector (40) comprises an anvil (60), a lower jaw (50), and a staple cartridge (70) received by lower jaw (50).

FIGS. 17 and 18 also illustrate an exemplary buttress applicator (200). Buttress applicator (200) is configured to selectively retain buttress assemblies (100). In the present example, buttress assembly (100) is selectively retained on a top side of applicator (200) and another buttress assembly (100) is selectively retained on a bottom side of applicator (200). In some other versions, applicator (200) can be configured such that only one buttress assembly (100) is selectively retained by buttress applicator (200).

To use buttress applicator (200) to load end effector (40) with buttress assemblies (100), the operator would first position applicator (200) and end effector (40) such that end effector (40) is aligned with an open end (202) of applicator (200) as shown in FIG. 17. The operator would then advance end effector (40) distally (and/or retract applicator (200) proximally) to position buttress assemblies (100) between anvil (60) and staple cartridge (70) as shown in FIG. 18. In order to load buttress assemblies (100) on end effector (40), the operator may simply close end effector (40) by pivoting anvil (60) toward staple cartridge (70). Closure of end effector (40) results in the distal ends of anvil (60) and staple cartridge (70) bearing against retaining features of buttress applicator (200) that are configured to selectively retain buttress assemblies (100) with buttress applicator (200). This contact deflects such retaining features of buttress applicator (200) to thereby permit contact between a surface of anvil (60) and buttress assembly (100) on one side of buttress applicator (200), and a surface of staple cartridge (70) and buttress assembly (100) on another side of buttress applicator (200). Buttress assemblies (100) comprise an adhesive on their respective surfaces such that with end effector (40) clamping on both buttress assemblies (100), buttress assemblies (100) are adhered respectively to an underside of anvil (60) and a deck surface of staple cartridge (70). End effector (40) may then be re-opened (i.e., pivoting anvil (60) away from staple cartridge (70)) and pulled away from buttress applicator (200). With retaining features of applicator (200) disengaged from buttress assemblies (100), end effector (40) may freely pull buttress assemblies (100) away from buttress applicator (200) as end effector (40) is pulled away from buttress applicator (200). With buttress assemblies (100) loaded on end effector (40), end effector (40) may then be used to cut, staple, and reinforce the tissue site.

In addition to the foregoing, it should also be understood that any of the various buttress assemblies described herein may be further constructed and operable in accordance with at least some of the teachings of U.S. Pat. Pub. No. 2016/0278774, entitled "Method of Applying a Buttress to a Surgical Stapler," published Sep. 29, 2016, the disclosure of which is incorporated by reference herein.

IV. EXEMPLARY METHOD OF PACKAGING A BUTTRESS APPLICATOR

Figure 19:
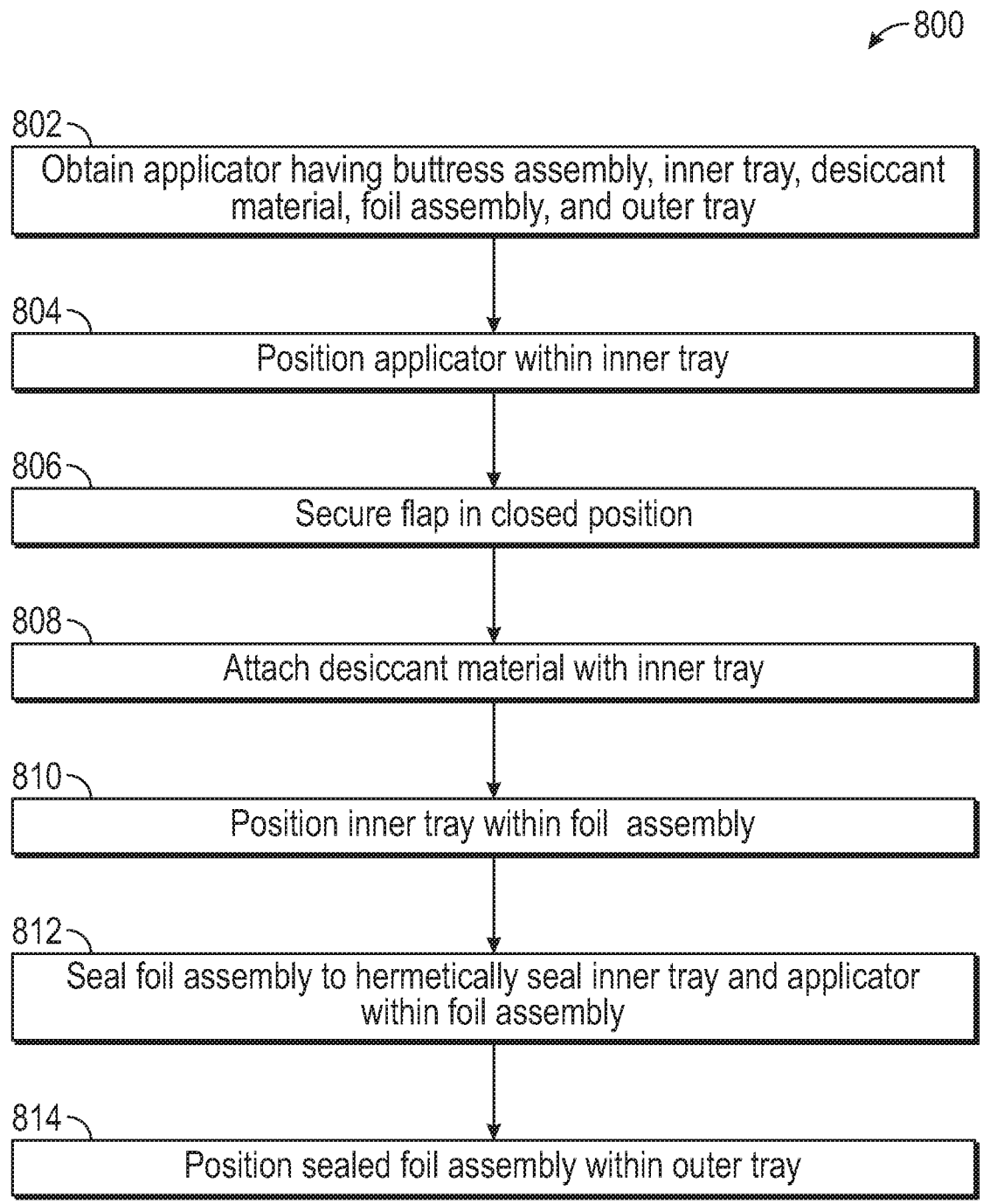
FIG. 19 depicts a schematic view of an exemplary method for packaging an applicator having a buttress assembly for use with a surgical stapler.

FIG. 19 schematically illustrates an exemplary method for packaging a buttress applicator (800) such as buttress applicators (200, 300) described above. At step (802), applicator (300) with buttress assemblies (316, 318) is obtained, along with inner tray (600), desiccant material (604), foil assembly (400), and outer tray (500). At step (804), applicator (300) is positioned within inner tray (600). In some instances this includes positioning applicator (300) is a specific orientation relative to base (606) of inner tray (600) so that applicator (300) sits flat within base (606) of inner tray (600) and allows flap (602) to properly and fully close. At step (806), flap (602) is secured in the closed position by engaging fastening features (609). At step (808), desiccant material (604) is attached with area (624) of inner tray (600) and selectively secured by tabs (632). At step (810), inner tray (600) is positioned within foil assembly (400). In particular, inner tray (600) may be placed between top and bottom layers (402, 404) of foil assembly (400). At step (812), foil assembly (400) is sealed to hermetically seal inner tray (600) and applicator (300) within foil assembly (400). At step (814) sealed foil assembly (400) containing inner tray (600)

with applicator (300) is positioned within outer tray (500), where outer tray (500) is configured to protect foil assembly (400) from damage.

While the above steps describe one exemplary packaging method, other methods may be used, or modifications to method (800) may be made as will be apparent to those of ordinary skill in the art in view of the teachings herein. For instance, the order of the steps of method (800) as shown and described above are not required in all versions. For instance, where practical or convenient or desired, certain steps can be completed before others such that the above shown and described steps should not be considered limited to their presented sequential order. Still other modifications may involve adding or omitting certain steps.

V. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A packaging assembly for an applicator is configured for loading a buttress assembly onto an end effector of a surgical stapler. The packaging assembly comprises: (a) an outer tray; (b) a pouch having a top layer, a bottom layer, and an interior between the top and bottom layers, wherein the top layer and the bottom layer are connectable to form a selective hermetic seal around the interior, and wherein the bottom layer of the pouch is configured to be contacted by the outer tray; (c) an inner tray configured to be positionable within the interior of the pouch such that the bottom layer of the pouch separates the inner tray from the outer tray; and (d) a desiccant material, wherein the inner tray is configured to selectively retain the desiccant material, wherein the desiccant material is configured to absorb any moisture within the interior of the pouch.

Example 2

The packaging assembly of Example 1, wherein the outer tray is configured to protect the bottom layer of the pouch from damage by fitting closely against the bottom layer of the pouch.

Example 3

The packaging assembly of any one or more of Examples 1 through 2, wherein the pouch is made of foil.

Example 4

The packaging assembly of any one or more of Examples 1 through 3, wherein the top layer of the pouch and the bottom layer of the pouch are each configured to closely follow the contour of the inner tray so as to protect the pouch from damage.

Example 5

The packaging assembly of any one or more of Examples 1 through 4, wherein the inner tray is further configured to selectively retain the applicator.

Example 6

The packaging assembly of any one or more of Examples 1 through 5, wherein the inner tray comprises a base, a flap, and a living hinge connecting the flap with the base.

Example 7

The packaging assembly of Example 6, wherein the base is configured to selectively retain the applicator, and wherein the flap is configured to rotate from a closed position to an open position, wherein in the closed position the flap at least partially covers the applicator when the applicator is selectively retained within the base.

Example 8

The packaging assembly of any one or more of Examples 6 through 7, wherein the inner tray further comprises at least one fastening feature configured to selectively connect the flap with the base.

Example 9

The packaging assembly of Example 8, wherein the at least one fastening feature comprises first and second fastening members configured to engage one another when the flap is in the closed position when the applicator is properly positioned within the base, and wherein the first and second fastening members are further configured to not engage one another when the applicator is improperly positioned within the base.

Example 10

The packaging assembly of any one or more of Examples 1 through 9, wherein the inner tray is configured such that a first end of the applicator is only positionable within the tray facing one way.

Example 11

The packaging assembly of any one or more of Examples 1 through 10, wherein the inner tray comprises an area on an outer surface of the inner tray, wherein the area is configured to selectively retain the desiccant material such that the desiccant material does not contact the applicator.

Example 12

The packaging assembly of any one or more of Examples 1 through 11, wherein the inner tray comprises a base configured to selectively retain the applicator, and wherein the inner tray comprises a flap connectable with the base, wherein when the flap is in a closed position the flap is configured to shield a buttress assembly of the applicator so that the buttress assembly is inaccessible.

Example 13

The packaging assembly of any one or more of Examples 1 through 12, wherein the inner tray comprises a flap having a peninsula portion configured for grasping when opening the flap.

Example 14

The packaging assembly of any one or more of Examples 1 through 13, wherein the inner tray comprises a molded plastic.

Example 15

The packaging assembly of any one or more of Examples 1 through 14, wherein the desiccant material comprises a paperboard.

Example 16

A packaging assembly for one or more buttresses is configured for use with a surgical stapler. The packaging assembly comprises (a) an outer tray, and (b) an inner tray configured to selectively retain an applicator. The applicator is configured for selectively retaining the one or more buttresses, and for loading the one or more buttresses onto an end effector of the surgical stapler. The packaging assembly further comprises (c) an impermeable material positionable between the outer tray and the inner tray. The impermeable material surrounds the applicator selectively retained by the inner tray forming a hermetic seal around the inner tray and applicator.

Example 17

The packaging assembly of Example 16, wherein the outer tray is configured to protect the impermeable material from damage.

Example 18

A method for packaging an applicator having a buttress assembly configured to be loaded onto an end effector of a surgical stapler. The method comprising: (a) positioning the applicator within a base of an inner tray; (b) securing a movable flap in a closed positioned, wherein in the closed position the movable flap is retained against the base of the inner tray by one or more fastening features; (c) positioning the inner tray with the applicator between a first foil layer and a second foil layer; and (d) attaching the first foil layer with the second foil layer to define a foil assembly that surrounds the inner tray with the applicator to create a hermetic seal around the inner tray with the applicator.

Example 19

The method of Example 18, further comprising positioning the foil assembly containing the inner tray with the applicator within an outer tray configured to prevent damage to the foil assembly.

Example 20

The method of any one or more of Examples 18 through 19, wherein positioning the applicator within a base of the inner tray comprises orienting the applicator in one direction so that the applicator sits flat within the base of the inner tray and allows the flap to properly close.

VI. MISCELLANEOUS

While the terms "buttress" and "buttress assembly" are used throughout this disclosure, it should be understood that the term is not intended to limit the scope of the present invention in any way. For instance, use of the terms "buttress" and "buttress assembly" is not intended to demonstrate contemplation that a "buttress" or "buttress assembly" can only be used to provide structural support to a staple line or serve any other particular purpose. It is contemplated that "buttress" or "buttress assembly" may serve a variety of purposes in addition to or as an alternative to providing structural support to a staple line. The terms "buttress" and "buttress assembly" should therefore be read broadly to include any kind of adjunct to a staple line that serves any suitable purpose.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

In addition to the foregoing, it should also be understood that any of the various buttress assemblies described herein may be further constructed and operable in accordance with at least some of the teachings of U.S. Pat. Pub. No. 2016/0278774, entitled "Method of Applying a Buttress to a Surgical Stapler," published Sep. 29, 2016, issued as U.S. Pat. No. 10,349,939 on Jul. 16, 2019, the disclosure of which is incorporated by reference herein; U.S. Pat. Pub. No. 2017/0049444, entitled "Implantable Layers for a Surgical Instrument," published Feb. 23, 2017, issued as U.S. Pat. No. 10,385,249 on Nov. 17, 2020, the disclosure of which is incorporated by reference herein; U.S. Pat. Pub. No. 2017/0086837, entitled "Compressible Adjunct with Crossing Spacer Fibers," published Mar. 30, 2017, issued as U.S. Pat. No. 10,433,846 on Oct. 8, 2019, the disclosure of which is incorporated by reference herein; and U.S. Pat. Pub. No. 2017/0086842, entitled "Method for Applying an Implantable Layer to a Fastener Cartridge," issued Mar. 30, 2017, the disclosure of which is incorporated by reference herein. Furthermore, in addition to the methods described herein, any of the various buttress assemblies described herein may be applied to end effector (40) in accordance with at least some of the teachings of U.S. Pat. Pub. No. 2017/0056016, entitled "Surgical Stapler Buttress Applicator with End Effector Actuated Release Mechanism," published Mar. 2, 2017, issued as U.S. Pat. No. 10,342,542 on Jul. 9, 2019, the disclosure of which is incorporated by reference herein; U.S. Pat. Pub. No. 2017/0056017, entitled "Surgical Stapler Buttress Applicator with Multi-Zone Platform for Pressure Focused Release," published Mar. 2, 2017, issued as U.S. Pat. No. 10,639,039 on May 5, 2020, the disclosure of which is incorporated by reference herein; U.S. Pat. Pub. No. 2017/0055980, entitled "Surgical Stapler Buttress Applicator with Spent Staple Cartridge Lockout," published Mar. 2, 2017, issued as U.S. Pat. No. 11,039,832 on Jun. 22, 2021, the disclosure of which is incorporated by reference herein; U.S. Pat. Pub. No. 2017/0056018, entitled "Surgical Stapler Buttress Applicator with State Indicator," published Mar. 2, 2017, issued as U.S. Pat. No. 10 349,940 on Jul. 16, 2019, the disclosure of which is incorporated by reference herein; U.S. Pat. Pub. No. 2017/0055982, entitled "Surgical Stapler Buttress Applicator with Multi-Point Actuated Release Mechanism," published Mar. 2, 2017, issued as U.S. Pat. No. 10,342,532 on Jul. 9, 2019, the disclosure of which is incorporated by reference herein; U.S. Pat. Pub. No. 2017/0055981, entitled "Method of Applying a Buttress to a Surgical Stapler End Effector," published Mar. 2, 2017, issued as U.S. Pat. No. 10,166,023 on Jan. 1, 2019, the disclosure of which is incorporated by reference herein; and/or U.S. Pat Pub. No. 2017/0086842, entitled "Method for Applying an Implantable Layer to a Fastener Cartridge," published Mar. 30, 2017, the disclosure of which is incorporated by reference herein. Various suitable ways in which the teachings herein may be combined with various teachings of the above-cited references will be apparent to those of ordinary skill in the art.

It should also be understood that the teachings herein may be readily combined with various teachings in U.S. patent application Ser. No. 16/235,473, entitled "Adhesive Distribution on Buttress for Surgical Stapler," filed on Dec. 28, 2018, published as U.S. Pub. No. 2020/0205820 on Jul. 2, 2020, the disclosure of which is incorporated by reference herein. Various suitable ways in which the teachings herein may be combined with the teachings of U.S. patent application Ser. No. 16/235,473, published as U.S. Pub. No. 2020/0205820 on Jul. 2, 2020, will be apparent to those of ordinary skill in the art.

It should also be understood that the teachings herein may be readily combined with various teachings in U.S. patent application Ser. No. 16/235,488, entitled "Configuration of Buttress for Surgical Stapler," filed on Dec. 28, 2018 published as U.S. Pub. No. 2020/0205821 on Jul. 2, 2020, the disclosure of which is incorporated by reference herein. Various suitable ways in which the teachings herein may be combined with the teachings of U.S. patent application Ser. No. 16/235,488, published as U.S. Pub. No. 2020/0205821 on Jul. 2 2020, will be apparent to those of It should also be understood that the teachings herein may be readily combined with various teachings in U.S. patent application Ser. No. 16/235,503, entitled "Surgical Stapler Buttress with Tissue In-Growth Promotion," filed on Dec. 28, 2018, published as U.S. Pub. No. 2020/0205822 on Jul. 2, 2020, the disclosure of which is incorporated by reference herein. Various suitable ways in which the teachings herein may be combined with the teachings of U.S. patent application Ser. No. 16/235,503, published as U.S. Pub. No. 2020/0205822 on Jul. 2, 2020, will be apparent to those of ordinary skill in the art.

It should also be understood that the teachings herein may be readily combined with various teachings in U.S. patent application Ser. No. 16/235,522, entitled "Applicator for Surgical Stapler Buttress," filed on Dec. 28, 2018, published as U.S. Pub. No. 2020/0205823 on Jul. 2, 2020, the disclosure of which is incorporated by reference herein. Various suitable ways in which the teachings herein may be combined with the teachings of U.S. patent application Ser. No. 16/235,522, published as U.S. Pub. No. 2020/0205823 on Jul. 2, 2020, will be apparent to those of ordinary skill in the art.

It should also be understood that the teachings herein may be readily combined with various teachings in U.S. patent application Ser. No. 29/675,168, entitled "Applicator for Surgical Stapler Buttress," filed on Dec. 28, 2018, issued as U.S. Pat. No. D901,686 on Nov. 10, 2020, the disclosure of which is incorporated by reference herein. Various suitable ways in which the teachings herein may be combined with the teachings of U.S. patent application Ser. No. 29/675,168, issued as U.S. Pat. No. D901,686 on Nov. 10, 2020, will be apparent to those of ordinary skill in the art.

It should also be understood that the teachings herein may be readily combined with various teachings in U.S. patent application Ser. No. 29/675,170, entitled "Buttress for Surgical Stapler," filed on Dec. 28, 2018, the disclosure of which is incorporated by reference herein. Various suitable ways in which the teachings herein may be combined with the teachings of U.S. patent application Ser. No. 29/675,170 will be apparent to those of ordinary skill in the art.

It should also be understood that the teachings herein may be readily combined with various teachings in U.S. patent application Ser. No. 29/675,172, entitled "Tray for Surgical Stapler Buttress Applicator," filed on Dec. 28, 2018, issued as U.S. Pat. No. D922,576 on Jun. 15, 2021, the disclosure of which is incorporated by reference herein. Various suitable ways in which the teachings herein may be combined with the teachings of U.S. patent application Ser. No. 29/675,172, issued as U.S. Pat. No. D922,576 on Jun. 15, 2021, will be apparent to those of ordinary skill in the art.

It should also be understood that the teachings herein may be readily combined with various teachings in U.S. patent application Ser. No. 16/235,617, entitled "Method of Applying Buttresses to Surgically Cut and Stapled Sites," filed on Dec. 28, 2018, issued as U.S. Pat. No. 11,033,269 on Jun. 15, 2021; the disclosure of which is incorporated by reference herein. Various suitable ways in which the teachings herein may be combined with the teachings of U.S. patent application Ser. No. 16/235,617, issued as U.S. Pat. No. 11,033,269 on Jun. 15, 2021, will be apparent to those of ordinary skill in the art.

It should also be understood that the teachings herein may be readily combined with various teachings in U.S. patent application Ser. No. 16/235,630, entitled "Curved Tip Surgical Stapler Buttress Assembly Applicator with Opening Feature for Curved Tip Alignment," filed on Dec. 28, 2018, published as U.S. Pub. No. 2020/0205826 on Jul. 2, 2020; the disclosure of which is incorporated by reference herein. Various suitable ways in which the teachings herein may be combined with the teachings of U.S. patent application Ser. No. 16/235,630, published as U.S. Pub. No. 2020/0205826 on Jul. 2, 2020, will be apparent to those of ordinary skill in the art.

It should also be understood that the teachings herein may be readily combined with various teachings in U.S. patent application Ser. No. 16/235,670,entitled "Curved Tip Surgical Stapler Buttress Assembly Applicator with Proximal Alignment Features," filed on Dec. 28, 2018, issued as U.S. Pat. No. 10,905,424 on Feb. 2, 2021; the disclosure of which is incorporated by reference herein. Various suitable ways in which the teachings herein may be combined with the teachings of U.S. patent application Ser. No. 16/235,670, issued as U.S. Pat. No. 10,905,424 on Feb. 2, 2021, will be apparent to those of ordinary skill in the art.

It should also be understood that the teachings herein may be readily combined with various teachings in U.S. patent application Ser. No. 16/235,681, entitled "Curved Tip Surgical Stapler Buttress Assembly Applicator with Compression Layer Pocket Feature," filed on Dec. 28, 2018, issued as U.S. Pub. No. 2020/0205807 on Jul. 2, 2020; the disclosure of which is incorporated by reference herein. Various suitable ways in which the teachings herein may be combined with the teachings of U.S. patent application Ser. No. 16/235,681, issued as U.S. Pub. No. 2020/0205807 on Jul. 2, 2020, will be apparent to those of ordinary skill in the art.

It should also be understood that the teachings herein may be readily combined with various teachings in U.S. patent application Ser. No. 29/675,197, entitled "Applicator for a Surgical Stapler Buttress," filed on Dec. 28, 2018, issued as U.S. Pat. No. D903,115 on Nov. 24, 2020; the disclosure of which is incorporated by reference herein. Various suitable ways in which the teachings herein may be combined with the teachings of U.S. patent application Ser. No. 29/675,197, issued as U.S. Pat. No. D903,115 on Nov. 24, 2020, will be apparent to those of ordinary skill in the art.

It should also be understood that the teachings herein may be readily combined with various teachings in U.S. patent application Ser. No. 29/675,199, entitled "Buttress Assembly for a Surgical Stapler," filed on Dec. 28, 2019; the disclosure of which is incorporated by reference herein. Various suitable ways in which the teachings herein may be combined with the teachings of U.S. patent application Ser. No. 29/675,199, will be apparent to those of ordinary skill in the art.

It should be appreciated that any patent, publication, or other disclusure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclusure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A packaging assembly for an applicator configured for loading a buttress assembly onto an end effector of a surgical stapler, wherein the packaging assembly comprises:
    (a) an outer tray;
    (b) a pouch having a top layer, a bottom layer, and an interior between the top and bottom layers, wherein the top layer and the bottom layer are connectable to form a selective hermetic seal around the interior, and wherein the bottom layer of the pouch is configured to be contacted by the outer tray;
    (c) an inner tray configured to be positionable within the interior of the pouch such that the bottom layer of the pouch separates the inner tray from the outer tray, wherein the inner tray includes a base and a flap hingedly coupled with the base, wherein the base is configured to retain the applicator, wherein the flap is rotatable relative to the base between a closed position and an open position, wherein the flap in the closed position is configured to expose at least a portion of the applicator within the base; and
    (d) a desiccant material, wherein the flap of the inner tray is configured to selectively retain the desiccant material in a position on an outer surface of the flap that inhibits contact between the desiccant material and the applicator, wherein the desiccant material is configured to absorb any moisture within the interior of the pouch.

2. The packaging assembly of claim 1, wherein the outer tray is configured to protect the bottom layer of the pouch from damage by fitting closely against the bottom layer of the pouch.

3. The packaging assembly of claim 1, wherein the pouch is made of foil.

4. The packaging assembly of claim 1, wherein the top layer of the pouch and the bottom layer of the pouch are each configured to closely follow the contour of the inner tray so as to protect the pouch from damage.

5. The packaging assembly of claim 1, wherein the inner tray is further configured to selectively retain the applicator.

6. The packaging assembly of claim 1, wherein the inner tray further includes a living hinge connecting the flap with the base.

7. The packaging assembly of claim 1, wherein in the closed position the flap at least partially covers the applicator when the applicator is selectively retained within the base.

8. The packaging assembly of claim 1, wherein the inner tray further comprises at least one fastening feature configured to selectively connect the flap with the base.

9. The packaging assembly of claim 8, wherein the at least one fastening feature comprises first and second fastening members configured to engage one another when the flap is in the closed position when the applicator is properly positioned within the base, and wherein the first and second fastening members are further configured to not engage one another when the applicator is improperly positioned within the base.

10. The packaging assembly of claim 1, wherein the inner tray is configured such that a first end of the applicator is only positionable within the inner tray facing one way.

11. The packaging assembly of claim 1, wherein the desiccant material includes a plurality of engagement features configured to selectively retain the desiccant material such that the desiccant material does not contact the applicator.

12. The packaging assembly of claim 1, wherein when the flap is in the closed position the flap is configured to shield a buttress assembly of the applicator so that the buttress assembly is inaccessible.

13. The packaging assembly of claim 1, wherein the flap has a peninsula portion configured for grasping when opening the flap.

14. The packaging assembly of claim 1, wherein the inner tray comprises a molded plastic.

15. A packaging assembly for one or more buttresses configured for use with a surgical stapler, wherein the packaging assembly comprises:
   (a) an outer tray;
   (b) an inner tray configured to selectively retain an applicator, wherein the applicator is configured for selectively retaining the one or more buttresses, and for loading the one or more buttresses onto an end effector of the surgical stapler, wherein the inner tray includes a base and a flap hingedly coupled with the base, wherein the base is configured to selectively retain the applicator, wherein the flap has a guide feature configured to engage and maintain the applicator in a longitudinally aligned orientation in which an open end of the applicator is aligned with a proximal end of the base, wherein the guide feature is configured to prevent the flap from closing fully against the base when the applicator is not in the longitudinally aligned orientation; and
   (c) an impermeable material positionable between the outer tray and the inner tray, wherein the impermeable material surrounds the applicator selectively retained by the inner tray forming a hermetic seal around the inner tray and applicator.

16. The packaging assembly of claim 15, wherein the outer tray is configured to protect the impermeable material from damage.

17. A method for packaging an applicator having a buttress assembly configured to be loaded onto an end effector of a surgical stapler, the method comprising:
   (a) positioning the applicator within a base of an inner tray such that a proximal end of the applicator is longitudinally aligned with a guide feature of a movable flap;
   (b) securing the movable flap in a closed position relative to the base, wherein in the closed position the movable flap is retained against the base of the inner tray by one or more mechanical fastening features, wherein the one or more mechanical fastening features includes first and second mechanical fastening members that releasably engage one another in the closed position with the applicator properly positioned within the base;
   (c) positioning the inner tray with the applicator between a first foil layer and a second foil layer; and
   (d) attaching the first foil layer with the second foil layer to define a foil assembly that surrounds the inner tray with the applicator to create a hermetic seal around the inner tray with the applicator.

18. The method of claim 17, further comprising positioning the foil assembly containing the inner tray with the applicator within an outer tray configured to prevent damage to the foil assembly.

19. The method of claim 17, wherein positioning the applicator within the base of the inner tray comprises orienting the applicator in one direction so that the applicator sits flat within the base of the inner tray and allows the moveable flap to properly close.

20. The packaging assembly of claim 11, wherein an outer surface of the flap includes a plurality of openings configured to engage the plurality of engagement features to selectively retain the desiccant material.

* * * * *